United States Patent
Albayrak et al.

(10) Patent No.: US 9,255,255 B2
(45) Date of Patent: Feb. 9, 2016

(54) SYNTHESIS OF LINEAR AND BRANCHED POLYMERS OF POLYPEPTIDES THROUGH DIRECT CONJUGATION

(71) Applicant: The Board of Trustees of the Leland Stanford Junior University, Palo Alto, CA (US)

(72) Inventors: Cem Albayrak, Mountain View, CA (US); James R. Swartz, Menlo Park, CA (US); Yuan Lu, Palo Alto, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 9 days.

(21) Appl. No.: 14/196,851

(22) Filed: Mar. 4, 2014

(65) Prior Publication Data

US 2014/0315276 A1    Oct. 23, 2014

Related U.S. Application Data

(60) Provisional application No. 61/772,447, filed on Mar. 4, 2013.

(51) Int. Cl.
| | |
|---|---|
| *C12N 7/00* | (2006.01) |
| *C07K 14/005* | (2006.01) |
| *C12P 21/00* | (2006.01) |
| *C12P 21/02* | (2006.01) |
| *C07K 1/107* | (2006.01) |

(52) U.S. Cl.
CPC ............... *C12N 7/00* (2013.01); *C07K 1/1075* (2013.01); *C07K 14/005* (2013.01); *C12P 21/02* (2013.01)

(58) Field of Classification Search
None
See application file for complete search history.

(56) References Cited

U.S. PATENT DOCUMENTS

| | | | |
|---|---|---|---|
| 6,337,191 B1 | 1/2002 | Swartz et al. | |
| 7,045,337 B2 | 5/2006 | Schultz et al. | |
| 7,375,234 B2 | 5/2008 | Sharpless et al. | |
| 7,718,410 B2 | 5/2010 | Deiters et al. | |
| 8,030,074 B2 | 10/2011 | Schultz et al. | |
| 2004/0209321 A1 | 10/2004 | Swartz et al. | |
| 2005/0054032 A1 | 3/2005 | Voloshin et al. | |
| 2005/0054044 A1 | 3/2005 | Swartz et al. | |
| 2007/0003925 A1* | 1/2007 | Nolte et al. ........................ 435/5 |
| 2008/0311412 A1 | 12/2008 | Fokin et al. | |
| 2014/0315276 A1* | 10/2014 | Albayrak et al. .......... 435/235.1 |

FOREIGN PATENT DOCUMENTS

| | | |
|---|---|---|
| WO | 2004/016778 A1 | 2/2004 |
| WO | 2005/052117 A2 | 6/2005 |

OTHER PUBLICATIONS

Strable et al. (Bioconjugate Chemistry. 2008; 19: 866-875).*
Albayrak, "Using *E. coli*-based cell-free protein synthesis to evaluate the kinetic performance of an orthogonal tRNA and aminoacyl-tRNA synthetase pair." Biochem Biophys Res Commun. (Feb. 8, 2013), 431(2):291-5.
Adzima, "Spatial and temporal control of the alkyne-azide cycloaddition by photoinitiated Cu(II) reduction" Nature Chemistry (2011), (3):258-261.
Baskin, "Copper-free click chemistry for dynamic in vivo imaging", Proceedings of the National Academy of Sciences of the United States of America, (2007), 130, 16793-16797.
Budyka, "Photochemistry of Aromatic Azides and Nitrenes" High Energy Chemistry (2007), 41, 176-187.
Bundy, "Site-specific incorporation of p-propargyloxyphenylalanine in a cell-free environment for direct protein-protein click conjugation." Bioconjug Chem. (Feb. 17, 2010), 21(2):255-63.
Calhoun, "An economical method for cell-free protein synthesis using glucose and nucleoside monophosphates." Biotechnol Prog. (Jul.-Aug. 2005), 21(4)1146-53.
Calhoun, "Total amino acid stabilization during cell-free protein synthesis reactions." J Biotechnol. (May 17, 2006), 123(2):193-203.
Chin; et al. "Addition of p-azido-L-phenylalanine to the genetic code of *Escherichia coli*", J Am Chem Soc. (Aug. 7, 2002), 124(31):9026-7.
Cho; "Optimized clinical performance of growth hormone with an expanded genetic code", Proceedings of he National Academy of Sciences of the United States of America (May 2011), 108(22):9060-9065.
Codelli, "Second-generation difluorinated cyclooctynes for copper-free click chemistry", J Am Chem Soc. (Aug. 27, 2008), 130(34):11486-93.
Dueber, "Synthetic protein scaffolds provide modular control over metabolic flux.", Nat Biotechnol. (Aug. 27, 2009); (8):753-9.
Farrell; et al. "Photo-cross-linking interacting proteins with a genetically encoded benzophenone", Nat Methods. (May 2, 2005), (5):377-84.
Goerke, "Development of cell-free protein synthesis platforms for disulfide bonded proteins", Biotechnol Bioeng. (Feb. 1, 2008), 99(2):351-67.
Goerke, "High-level cell-free synthesis yields of proteins containing site-specific non-natural amino acids." Biotechnol Bioeng. (Feb. 1, 2009),102(2):400-16.

(Continued)

*Primary Examiner* — Shanon A Foley
(74) *Attorney, Agent, or Firm* — Bozicevic, Field & Francis LLP; Pamela J. Sherwood

(57) ABSTRACT

Methods are provided for a one step synthesis of polypeptide polymers or co-polymers. The polymers or co-polymers can be linear or branched. In the methods of the invention, the coding sequence for the polypeptide(s) to be polymerized is altered by introducing one or more codons for an nonnatural amino acid, which coding sequence is then utilized to produce the cognate polypeptide. The nonnatural amino acids are selected to be reactive with each other in a bioorthogonal reaction, and are combined in a conjugation reaction with the desired components of the polymer.

20 Claims, 12 Drawing Sheets
(10 of 12 Drawing Sheet(s) Filed in Color)

(56) References Cited

OTHER PUBLICATIONS

Hudalla, "Biomaterials that regulate growth factor activity via bioinspired interactions.", Adv Funct Mater. (May 24, 2011), 21(10):1754-1768.

Jewett, "Mimicking the *Escherichia coli* cytoplasmic environment activates long-lived and efficient cell-free protein synthesis" Biotechnol Bioeng. (Apr. 5, 2004), 86(1):19-26.

Johnson, "RF1 knockout allows ribosomal incorporation of unnatural amino acids at multiple sites", Nat Chem Biol, (Sep. 18, 2011), 7(11):779-86.

Laughlin, "In vivo imaging of membrane-associated glycans in developing zebrafish", Science. (May 2, 2008), 320 (5876):664-7.

Lin; et al. "Genetic reconstruction of the aerobic central metabolism in *Escherichia coli* for the absolute aerobic production of succinate.", Biotechnol Bioeng. (Jan. 20, 2005), 89(2):148-56.

Liu; et al. "A method for the generation of glycoprotein mimetics.", J Am Chem Soc. (Feb. 19, 2003),125(7):1702-3.

Magliery, "Unnatural Protein Engineering: Producing Proteins with Unnatural Amino Acids", Medicinal Chemistry Reviews (2005), 2:303-323.

Michel-Reydellet, "Amino acid stabilization for cell-free protein synthesis by modification of the *Escherichia coli* genome." Metab Eng. (Jul. 2004), 6(3):197-203.

Nguyen; et al., "Genetic encoding and labeling of aliphatic azides and alkynes in recombinant proteins via a pyrrolysyl-tRNA Synthetase/tRNA (CUA) pair and click chemistry.", J. Am. Chem. Soc. (Jul. 2009), 131(25):8720-1.

Nguyen; et al., "Genetically encoded 1,2-aminothiols facilitate rapid and site-specific protein labeling via a bio-orthogonal cyanobenzothiazole condensation." J. Am. Chem. Soc. (Aug. 2011), 133(3):11418-21.

Pedelacq, "Engineering and characterization of a superfolder green fluorescent protein." Nat Biotechnol. (Jan. 2006), 24(1):79-88.

Plass; et al., "Genetically encoded copper-free click chemistry.", Angew. Chem. Int. Ed. Engl. (Apr. 2011), 50 (17):3878-81.

Saxon, "Cell surface engineering by a modified Staudinger reaction.", Science (Mar. 17, 2000), 287(5460):2007-10.

Wang; et al. "Expanding the genetic code of *Escherichia coli*.", Science (Apr. 20, 2001), 292(5516):498-500.

Wang; et al. "Addition of the keto functional group to the genetic code of *Escherichia coli*.", Proc Natl Acad Sci U S A (Jan. 7, 2003), 100(1):56-61.

Wang, "Bioconjugation by copper(I)-catalyzed azide-alkyne [3+2] cycloaddition." J Am Chem Soc (Mar. 19, 2003), 125(11):3192-3.

Wang, "Expanding the genetic code.", Annu Rev Biophys Biomol Struct. (2006), 35:225-49.

Zawada; et al., "Microscale to manufacturing scale-up of cell-free cytokine production—a new approach for shortening protein production development timelines.", Biotechnol. Bioeng. (Jul. 2011), 108(7):1570-8.

\* cited by examiner

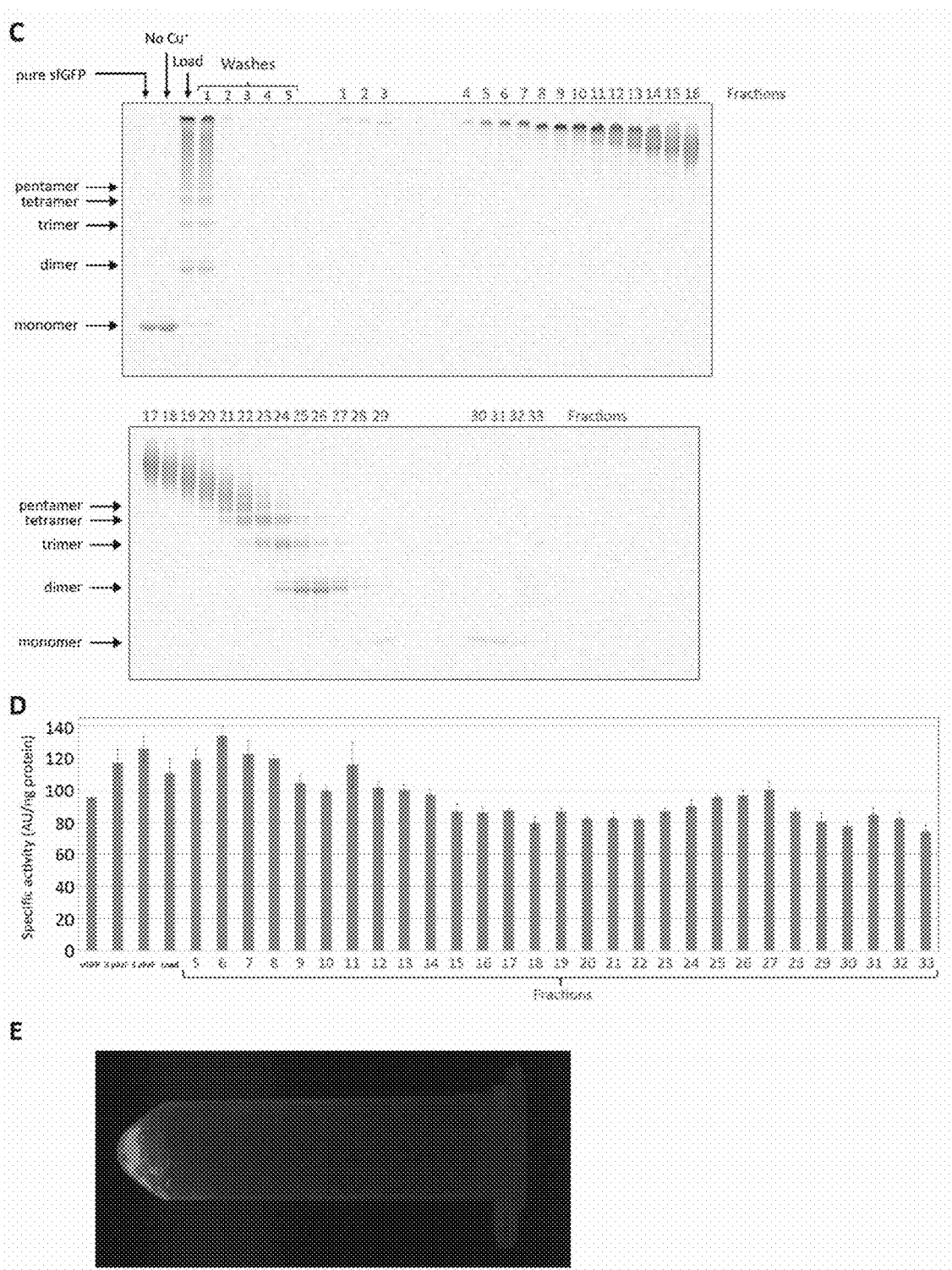
FIGURE 8 C-E

A  
+VLPs  
+Cu(I)

B  
+VLPs  
−Cu(I)

C  
−VLPs  
+Cu(I)

SEQUENCE LISTING

<160> NUMBER OF SEQ ID NOS: 6

<210> SEQ ID NO 1
<211> LENGTH: 149
<212> TYPE: PRT
<213> ORGANISM: Artificial Sequence
<220> FEATURE:
<223> OTHER INFORMATION: synthetic amino acid sequence

<400> SEQUENCE: 1

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

```
Thr Ala Ala Ala Leu Tyr Arg Asp Ala Leu Glu Ser Pro Glu His Cys
            35                  40                  45

Ser Pro His His Thr Ala Leu Arg Gln Ala Ile Leu Cys Trp Gly Asp
 50                  55                  60

Leu Met Thr Leu Ala Thr Trp Val Gly Thr Asn Leu Glu Asp Pro Ala
 65                  70                  75                  80

Ser Arg Asp Leu Val Val Ser Tyr Val Asn Thr Asn Val Gly Leu Lys
                 85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
130                 135                 140

Glu Thr Thr Val Val
145

<210> SEQ ID NO 2
<211> LENGTH: 453
<212> TYPE: DNA
<213> ORGANISM: Artificial Sequence
<220> FEATURE:
<223> OTHER INFORMATION: synthetic polynucleotide

<400> SEQUENCE: 2
atggatatcg acccgtacaa agaattcggc gcgaccgttg aactgctgtc tttcctgccg      60
tctgatttct ccccgtctgt tcgtgacctg ctggacaccg cggcagcact gtaccgtgac     120
gcgctggaat ctccggaaca ttgttctccg catcacactg cgctgcgtca ggcgattctg     180
tgctggggcg acctgatgac cctggcgact tgggttggca ccaacctgga agatccggcg     240
tctcgtgatc tggttgtttc ttacgttaac actaacgttg gtctgaaatt ccgtcagctg     300
ctgtggttcc acatctcttg cctgaccttc ggtcgtgaaa ccgttctgga ataccttggtt    360 tcttttggtg tttggattcg tactccgccg gcttaccgtc cgccgaacgc accgatcctg     420
agcaccctgc cggaaaccac tgttgtgtaa taa                                  453

<210> SEQ ID NO 3
<211> LENGTH: 149
<212> TYPE: PRT
<213> ORGANISM: Artificial Sequence
<220> FEATURE:
<223> OTHER INFORMATION: synthetic amino acid sequence
<220> FEATURE:
<221> NAME/KEY: MISC_FEATURE
<222> LOCATION: (76)..(76)
<223> OTHER INFORMATION: the amino acid at this position is
      azidohomoalanine

<400> SEQUENCE: 3

Met Asp Ile Asp Pro Tyr Lys Glu Phe Gly Ala Thr Val Glu Leu Leu
 1               5                  10                  15

Ser Phe Leu Pro Ser Asp Phe Pro Ser Val Arg Cys Leu Leu Asp
            20                  25                  30

Thr Ala Ala Ala Leu Tyr Arg Asp Ala Leu Glu Ser Pro Glu His Cys
            35                  40                  45

Ser Pro His His Thr Ala Leu Arg Gln Ala Ile Leu Cys Trp Gly Asp
 50                  55                  60

Leu Ser Thr Leu Ala Thr Trp Val Gly Thr Asn Xaa Glu Asp Pro Ala
 65                  70                  75                  80
```

```
Ser Arg Asp Leu Val Val Ser Tyr Val Asn Thr Asn Val Gly Leu Lys
            85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Cys Thr
            115                 120                 125

Pro Pro Ala Tyr Arg Pro Pro Asn Ala Pro Ile Leu Ser Thr Leu Pro
            130                 135                 140

Glu Thr Thr Val Val
145

<210> SEQ ID NO 4
<211> LENGTH: 453
<212> TYPE: DNA
<213> ORGANISM: Artificial Sequence
<220> FEATURE:
<223> OTHER INFORMATION: synthetic polynucleotide

<400> SEQUENCE: 4
atggatatcg acccgtacaa agaattcggc gcgaccgttg aactgctgtc tttcctgccg      60
tctgatttct ccccgtctgt tcgttgcctg ctggacaccg cggcagcact gtaccgtgac     120
gcgctggaat ctccggaaca ttgttctccg catcacactg cgctgcgtca ggcgattctg     180
tgctggggcg acctgagcac cctggcgact tgggttggca ccaacatgga agatccggcg     240
tctcgtgatc tggttgtttc ttacgttaac actaacgttg gtctgaaatt ccgtcagctg     300
ctgtggttcc acatctcttg cctgaccttc ggtcgtgaaa ccgttctgga atacctggtt     360
tcttttggtg tttggatttg tactccgccg gcttaccgtc cgccgaacgc accgatcctg     420
agcaccctgc cggaaaccac tgttgtgtaa taa                                 453

<210> SEQ ID NO 5
<211> LENGTH: 149
<212> TYPE: PRT
<213> ORGANISM: Artificial Sequence
<220> FEATURE:
<223> OTHER INFORMATION: synthetic amino acid sequence
<220> FEATURE:
<221> NAME/KEY: MISC_FEATURE
<222> LOCATION: (76)..(76)
<223> OTHER INFORMATION: the amino acid at this position is
      homopropargylglycine

<400> SEQUENCE: 5

Met Asp Ile Asp Pro Tyr Lys Glu Phe Gly Ala Thr Val Glu Leu Leu
1               5                   10                  15

Ser Phe Leu Pro Ser Asp Phe Pro Ser Val Arg Cys Leu Leu Asp
            20                  25                  30

Thr Ala Ala Ala Leu Tyr Arg Asp Ala Leu Glu Ser Pro Glu His Cys
            35                  40                  45

Ser Pro His His Thr Ala Leu Arg Gln Ala Ile Leu Cys Trp Gly Asp
            50                  55                  60

Leu Ser Thr Leu Ala Thr Trp Val Gly Thr Asn Xaa Glu Asp Pro Ala
65              70                  75                  80

Ser Arg Asp Leu Val Val Ser Tyr Val Asn Thr Asn Val Gly Leu Lys
            85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Cys Thr
            115                 120                 125
```

```
Pro Pro Ala Tyr Arg Pro Pro Asn Ala Pro Ile Leu Ser Thr Leu Pro
    130                 135                 140

Glu Thr Thr Val Val
145

<210> SEQ ID NO 6
<211> LENGTH: 453
<212> TYPE: DNA
<213> ORGANISM: Artificial Sequence
<220> FEATURE:
<223> OTHER INFORMATION: synthetic polynucleotide

<400> SEQUENCE: 6
atggatatcg acccgtacaa agaattcggc gcgaccgttg aactgctgtc tttcctgccg      60
tctgatttct tcccgtctgt tcgttgcctg ctggacaccg cggcagcact gtaccgtgac     120
gcgctggaat ctccggaaca ttgttctccg catcacactg cgctgcgtca ggcgattctg     180
tgctggggcg acctgagcac cctggcgact tgggttggca ccaacatgga agatccggcg     240
tctcgtgatc tggttgtttc ttacgttaac actaacgttg gtctgaaatt ccgtcagctg     300
ctgtggttcc acatctcttg cctgaccttc ggtcgtgaaa ccgttctgga atacctggtt     360
tcttttggtg tttggatttg tactccgccg gcttaccgtc cgccgaacgc accgatcctg     420
agcaccctgc cggaaaccac tgttgtgtaa taa                                 453
```

SYNTHESIS OF LINEAR AND BRANCHED POLYMERS OF POLYPEPTIDES THROUGH DIRECT CONJUGATION

BACKGROUND OF THE INVENTION

Protein synthesis is a fundamental biological process that underlies the development of polypeptide therapeutics, vaccines, diagnostics, and industrial enzymes. With the advent of recombinant DNA (rDNA) technology, it has become possible to harness the catalytic machinery of the cell to produce a desired protein. This can be achieved within the cellular environment or in vitro using extracts derived from cells.

Methods of recombinant protein synthesis include cell-free and cell-based methods of protein synthesis to introduce non-natural amino acids into a protein. For example, in vitro translation has been recognized for its ability to incorporate nonnatural and isotope-labeled amino acids as well as its capability to produce proteins that are unstable, insoluble, or cytotoxic in vivo. In addition, cell-free protein synthesis may play a role in revolutionizing protein engineering and proteomic screening technologies. The cell-free method bypasses the laborious processes required for cloning and transforming cells for the expression of new gene products in vivo, and is becoming a platform technology for this field.
Relevant Literature In vivo production of a green fluorescent protein containing multiple copies of pAzF is discussed in Johnson et al. (2011) *Nature Chemical Biology* 7:779-786. U.S. Pat. Nos. 7,375,234; 7,718,410; 8,030,074; 7,045,337. U.S. Patent Application 20080311412.

U.S. Pat. No. 6,337,191 B1; Swartz et al. U.S. Patent Published Application 20040209321; Swartz et al. International Published Application WO 2004/016778; Swartz et al. U.S. Patent Published Application 2005-0054032-A1; Swartz et al. U.S. Patent Published Application 2005-0054044-A1; Swartz et al. International Published Application WO 2005/052117. Calhoun and Swartz (2005) Biotechnol Bioeng 90(5):606-13; Jewett and Swartz (2004) Biotechnol Bioeng 86(1):19-26; Jewett et al. (2002) Prokaryotic Systems for In Vitro Expression. In: Weiner M, Lu Q, editors. Gene cloning and expression technologies. Westborough, Mass.: Eaton Publishing. p 391-411; Lin et al. (2005) Biotechnol Bioeng 89(2):148-56. (Wang et al. (2001) Science 292(5516):498-500; Wang et al. (2003) Proc Natl Acad Sci USA 100(1):56-61; Chin et al. (2002) J Am Chem Soc 124(31):9026-7; Farrell et al. (2005) Nat Methods, 2005. 2(5):377-84; Liu et al. (2003) J Am Chem Soc 125(7):1702-3, each herein specifically incorporated by reference

SUMMARY OF THE INVENTION

Methods are provided for a one step synthesis of multimeric polypeptide structures, including arrays, polymers or co-polymers. The arrays, polymers or co-polymers may, for example be linear, planar, icosahedral, branched, etc. In the methods of the invention, the coding sequence for the polypeptide(s) to be polymerized is altered by introducing one or more codons for an nonnatural amino acid, which coding sequence is then utilized to produce the cognate polypeptide. In some embodiments the polypeptide is synthesized in a cell free protein synthesis reaction (CFPS). In other embodiments the synthesis is performed in vivo. At least two different nonnatural amino acids are present in the monomers to be polymerized, where each different nonnatural amino acids may be present on a single polypeptide chain, or each may be present on different polypeptide chains. The nonnatural amino acids are selected to be reactive with each other in a bioorthogonal reaction. p-azido-L-phenylalanine (pAzF) and p-propargyloxy-L-phenylalanine (pPaF) are of particular interest for azide-alkyne cycloaddition. The polypeptide(s) thus produced may be purified prior to the coupling reaction, or may be reacted in the CFPS reaction mixture. Under conjugation conditions, in which the polypeptide subunits are introduced, the desired multimeric structure is formed.

In some embodiments the multimeric structure is comprised solely of one, two or more polypeptide subunits. In other embodiments the multimeric structure is comprised of one or more polypeptide subunits linked to small molecules, e.g. drugs, detectable moieties, and the like. In other embodiments the multimeric structure is comprised of one or more polypeptide subunits linked to small molecule polymers, e.g. polyethylene glycol, etc., for the synthesis of scaffolds and biomaterials where retention of protein activity is an important feature of the scaffold or biomaterial.

In some embodiments the multimeric structure is an array, e.g. a planar array; a virus-like particle (VLP), or the like, in which polypeptide monomers are covalently joined to form a two- or three-dimensional structure. In such multimeric structures, polypeptide monomers can be joined at two or more positions to form a cross-linked structure. Alternatively a naturally occurring multimeric structure, e.g. a VLP, can be strengthened with selective covalent bonds at 1 or more positions.

Compositions are also provided in which a plurality of polypeptide icosahedral assemblies are interconnected by covalent bonds. In such multimeric structures, two or more of the icosahedral structures are joined by covalent bonds, e.g. by the incorporation of non-natural amino acids capable of reacting to form covalent bonds, e.g. by click chemistry. In some embodiments the icosahedral structures are virus like particles. In some embodiments the VLPs themselves are stabilized by intercapsid bonds. In some specific embodiments, exemplary capsid proteins include the polypeptides of SEQ ID NO:1, in which mutations are introduced, e.g. M66S and L76M, to create bonds on the VLP surface; and/or in which mutations are introduced to stabilize the VLP with inter-capsid bonds, e.g. D29C and R127C. Exemplary polypeptides include, without limitation, those of SEQ ID NO:3 and SEQ ID NO:5.

In another embodiment, a multimeric structure of one, or of two different polypeptides are coupled to create novel scaffolds and biomaterials. In another embodiment the multimeric structures are conjugated to small molecules that comprise a reactive azido or alkyne moiety to form flexible and versatile multimeric structures, such as protein-coupled hydrogels for tissue engineering.

The site for introduction of the one or more non-natural amino acid(s) is generally selected to be surface-exposed, which provides a benefit of reducing steric limitations to improve attachment efficiency of the polypeptide. Where the polypeptide is an enzyme, site(s) for introduction of the one or more non-natural amino acid(s) are generally selected to be away from the active site, so that covalent coupling of the enzyme does not reduce enzymatic activity after polymerization. In some embodiments, the site(s) for introduction of the one or more non-natural amino acid(s) are selected to orient the active sites of the enzymes toward each other after conjugation, to minimize substrate diffusion distances and maximize substrate conversion.

The cell-free protein synthesis is performed with bacterial cell extracts from a polynucleotide template, where the reaction mixture comprises at least one orthogonal tRNA aminoacylated with an nonnatural amino acid, where the orthogonal tRNA base pairs with a codon that is not normally associated with an amino acid, e.g. a stop codon; a 4 bp codon, etc. The reaction mixture also comprises a tRNA synthetase capable of aminoacylating the orthogonal tRNA with an nonnatural amino acid. The orthogonal tRNA synthetase may be exogenously synthesized and added to the reaction mix prior to initiation of polypeptide synthesis. The orthogonal tRNA may be synthesized in the bacterial cells from which the cell extract is obtained, may be synthesized de novo during the polypeptide synthesis reaction, or may be exogenously added to the reaction mix.

In alternative embodiments the protein synthesis is performed in a cell, e.g. a microbial cell such as E. coli, etc. in which a system for introduction of nonnatural amino acids has been engineered.

A variety of polymer geometries are produced by the methods of invention, and include, without limitation: a head to tail linear polymer of one, two, or more different polypeptides; a branched polymer where multiple "arms" are conjugated to a single "base" polypeptide; and combinations thereof.

A benefit of the present invention is the ability to specifically place the covalent bond on the polypeptides that are to be coupled, thereby allowing the site to be selected so as to preserve biological function, e.g. enzymatic or binding activity. The methods find use in the coupling of various polypeptides. In one embodiment of the invention, two or more enzymes in a pathway of interest, e.g. a synthetic pathway, are covalently coupled, where the coupled enzymes increase substrate flux relative to the uncoupled enzymes. Such methods are also applicable to covalent joining of polypeptides in a regeneration or maturation pathway, e.g. where an enzyme that requires a cofactor or coenzyme is covalently joined for maximal holoenzyme activity.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE EMBODIMENTS

Figure 1:
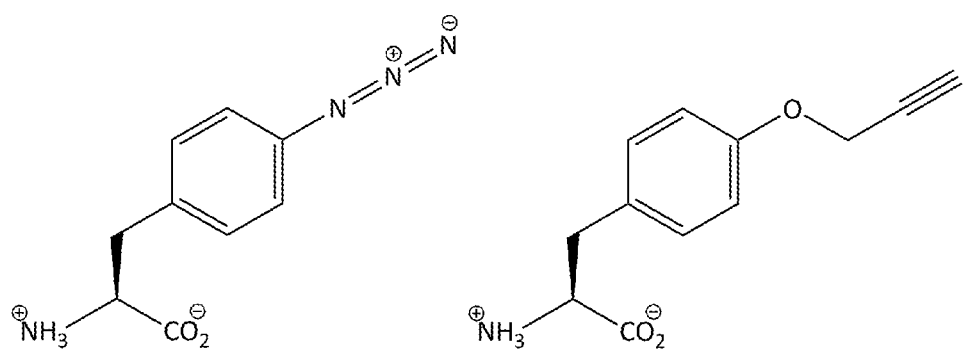
FIG. 1: Structures of the non-natural amino acids p-azido-L-phenylalanine (pAzF) and p-propargyloxy-L-phenylalanine (pPaF).
Figure 2:
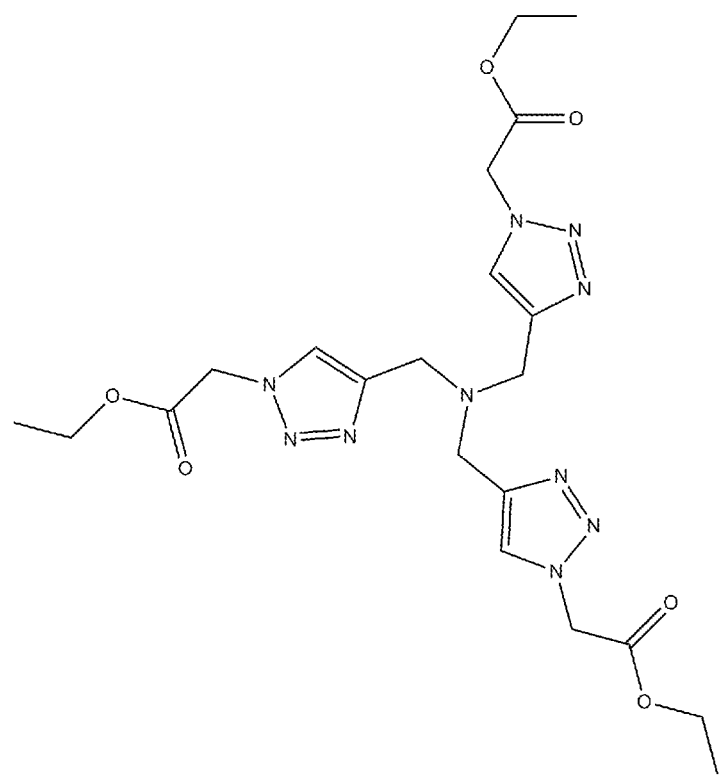
FIG. 2: Structure of the ligand tris(triazolylmethyl)amine (TTMA).

Methods are provided for a one step synthesis of linear or branched polypeptide multimeric structures. At least two different nonnatural amino acids are present in the monomers to be polymerized, where each different nonnatural amino acids may be present on a single polypeptide chain, or each may be present on different polypeptide chains. The nonnatural amino acids are selected to be reactive with each other in a bioorthogonal reaction. pAzF and pPaF are of particular interest, they enable the bioorthogonal azide-alkyne cycloaddition reaction. The polypeptide(s) thus produced may be purified prior to the coupling reaction.

As used herein, the term "one step synthesis" includes synthetic reactions that use gradual or sequential additions of the monomeric units or catalysts and enhancers; and synthesis reactions during which the concentrations of the reagents or reaction intermediates are increased by ultrafiltration or other means.

The target polypeptide(s) may be synthesized in a cell-free reaction mixture comprising at least one orthogonal tRNA aminoacylated with an nonnatural amino acid, where the orthogonal tRNA base pairs with a nonsense codon that is not normally associated with an amino acid, e.g. a stop codon; a 4 bp codon, etc. by methionine replacement, and the like as known in the art. Included in the methods are coupled transcription-translation reactions.

Alternatively in vivo protein synthesis is used to produce the polypeptides.

In one embodiment of the invention, the initial yield of active modified protein is at least about 50 μg/ml of reaction mixture; at least about 100 μg/ml of reaction mixture; at least about 250 μg/ml of reaction mixture; or more. A substantial portion of the target polypeptide thus produced contains the desired nonnatural amino acid, usually at least about 50%, at least about 75%, at least about 85%, at least about 95%, at least about 99%, or higher. The methods thus allow for high levels of multimeric structures to be produced.

A polypeptide subunit for the multimeric structure comprises at least one nonnatural amino acid at a pre-determined site, and may comprise or contain 1, 2, 3, 4, 5 or more nonnatural amino acids. If present at two or more sites in a single polypeptide, the nonnatural amino acids can be the same or different. Where the nonnatural amino acids are different on a single polypeptide, an orthogonal tRNA and cognate tRNA synthetase will be present for each nonnatural amino acid. Nonnatural amino acids include, without limitation, p-acetyl-phenylalanine, p-ethynyl-phenylalanine, p-propargyloxyphenylalanine, and p-azido-phenylalanine.

The methods of the present invention provide for proteins containing nonnatural amino acids that have biological activity comparable to the native protein. One may determine the specific activity of a protein in a composition by determining the level of activity in a functional assay, quantitating the amount of protein present in a non-functional assay, e.g. immunostaining, ELISA, quantitation on Coomassie or silver stained gel, etc., and determining the ratio of biologically active protein to total protein. Generally, the specific activity as thus defined will be at least about 5% that of the native protein, usually at least about 10% that of the native protein, and may be about 25%, about 50%, about 90% or greater.

The polypeptides synthesized by the methods of the invention provide the benefits of being able to attach any ligand (containing or not containing disulfide bonds) to the polypeptide through nonnatural amino acids covalently bonding to other nonnatural amino acids. Linkers may be used to link two similar or unique nonnatural amino acids, e.g. between two polypeptide chains. Site-specific post-translational modification at single or multiple sites using similar or different ligands may be conducted by but not limited by mild [3+2] cycloaddition reactions or ligand specific reactivity using a unique "ketone handle". Alternatively, an azido group can be linked to an alkyne where either is incorporated into the polypeptide surface and the other is part of a linker or ligand.

DEFINITIONS

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

The terms "desired protein" or "selected protein" are used interchangeably and refer generally to any peptide or protein having more than about 5 amino acids, which comprises at least one nonnatural amino acid, which nonnatural amino acid is encoded at a specific site in a protein coding polynucleotide. The polypeptides may be homologous to, or may be exogenous, meaning that they are heterologous, i.e., foreign, to the bacteria from which the bacterial cell-free extract is derived, such as a human protein, viral protein, yeast protein, etc. produced in the bacterial cell-free extract.

Examples of mammalian polypeptides include, but are not limited to, molecules such as renin; growth hormones, including human growth hormone; bovine growth hormone; growth hormone releasing factor; parathyroid hormone; thyroid stimulating hormone; lipoproteins; alpha-1-antitrypsin; insulin A-chain; insulin; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES and other chemokines; human macrophage inflammatory protein (MIP-1α); a serum albumin such as human serum albumin; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as αFGF and βFGF; epidermal growth factor (EGF); transforming growth factor (TGF) such as TGF-α and TGF-β, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-α, -β, and -γ; colony stimulating factors (CSFs), e.g., M-CSF, GM-CSF, and G-CSF; interleukins (ILs), e.g., IL-1 to IL-18; superoxide dismutase; T-cell receptors; surface membrane proteins; decay accelerating factor; viral antigen such as, for example, a portion of the AIDS envelope; transport proteins; homing receptors; addressins; regulatory proteins; antibodies; and fragments of any of the above-listed polypeptides.

Virus Like Particle.

As used herein, the term "virus like particle" refers to a stable macromolecular assembly of one or more virus proteins, usually viral coat proteins. The number of separate protein chains in a VLP will usually be at least about 60 proteins, about 80 proteins, at least about 120 proteins, or more, depending on the specific viral geometry. In the methods of the invention, the cell-free synthesis reaction mixture provides conditions permissive for self-assembly into the capsid structure, even where the concentration of coat proteins may be dilute relative to the concentrations associated with in vivo viral synthesis, e.g. less than about 500 µg/ml, less than about 400 µg/ml, less than about 250 µg/ml. The methods of the invention provide for synthesis of the coat protein in the absence of the virus polynucleotide genome, and thus the capsid may be empty, or contain non-viral components, e.g. mRNA fragments, etc. The cell-free synthesis reaction mixtures of the present invention surprisingly provide conditions permissive for self-assembly of coat proteins into a capsid structure displaying helical or icosahedral symmetry.

A stable VLP maintains the association of proteins in a capsid structure under physiological conditions for extended periods of time, e.g. for at least about 24 hrs, at least about 1 week, at least about 1 month, or more. Once assembled, the VLP can have a stability commensurate with the native virus particle, e.g. upon exposure to pH changes, heat, freezing, ionic changes, etc. Additional components of VLPs, as known in the art, can be included within or disposed on the VLP. VLPs do not contain intact viral nucleic acids, and they are non-infectious. In some embodiments there is sufficient viral surface envelope glycoprotein and/or adjuvant molecules on the surface of the VLP so that when a VLP preparation is formulated into an immunogenic composition and administered to an animal or human, an immune response (cell-mediated or humoral) is raised.

Viruses can be classified into those with helical symmetry or icosahedral symmetry. Generally recognized capsid morphologies include: icosahedral (including icosahedral proper, isometric, quasi-isometric, and geminate or "twinned"), polyhedral (including spherical, ovoid, and lemon-shaped), bacilliform (including rhabdo- or bullet-shaped, and fusiform or cigar-shaped), and helical (including rod, cylindrical, and filamentous); any of which may be tailed and/or may contain surface projections, such as spikes or knobs.

In one embodiment of the invention, the coat protein is selected from the capsids of viruses classified as having any icosahedral morphology, and the VLP has an icosahedral geometry. Generally, viral capsids of icosahedral viruses are composed of numerous protein sub-units arranged in icosahedral (cubic) symmetry. Native icosahedral capsids can be built up, for example, with 3 subunits forming each triangular face of a capsid, resulting in 60 subunits forming a complete capsid. A representative of this small viral structure is bacteriophage ØX174. Many icosahedral virus capsids contain more than 60 subunits. Many capsids of icosahedral viruses contain an antiparallel, eight-stranded beta-barrel folding motif. The motif has a wedge-shaped block with four beta strands (designated BIDG) on one side and four (designated CHEF) on the other. There are also two conserved alpha-helices (designated A and B), one is between betaC and betaD, the other between betaE and betaF.

Virus coat proteins of interest include any of the known virus type, e.g. dsDNA viruses, such as smallpox (variola); vaccinia; herpesviruses including varicella-zoster; HSV1, HSV2, KSVH, CMV, EBV; adenovirus; hepatitis B virus; SV40; T even phages such as T4 phage, T2 phage; lambda phage; etc. Single stranded DNA viruses include phiX-174; adeno-associated virus, etc. Negative-stranded RNA viruses include measles virus; mumps virus; respiratory syncytial virus (RSV); parainfluenza viruses (PIV); metapneumovirus; rabies virus; Ebola virus; influenza virus; etc. Positive-stranded RNA viruses include polioviruses; rhinoviruses; coronaviruses; rubella; yellow fever virus; West Nile virus; dengue fever viruses; equine encephalitis viruses; hepatitis A and hepatitis C viruses; tobacco mosaic virus (TMV); etc. Double-stranded RNA viruses include reovirus; etc. Retroviruses include rous sarcoma virus; lentiviruses such as HIV-1 and HIV-2; etc.

Bacteriophages are of interest, e.g. the MS2 bacteriophage, the Q beta bacteriophage, etc. Myoviridae (phages with contractile tails) include mu-like viruses; P1-like viruses, e.g. P1; phiW39, etc.; P2-like viruses; SPO-1-like viruses; T4-like viruses; etc. Podoviridae (phages with short tails) include N4-like viruses; P22-like viruses, e.g. P22; phi-29-like viruses, e.g. phi-29; T7-like viruses, e.g. T3; T7; W31; etc. Siphoviridae (phages with long non-contractile tails) include c2-like viruses; L5-like viruses; Lambda-like viruses, e.g. phage lambda, HK022; HK97, etc.; N15-like viruses; PhiC31-like viruses; psiM1-like viruses; T1-like viruses, e.g. phage T1, etc. Microviridae (isometric ssDNA phages) include Chlamydiamicrovirus; Microvirus, e.g. phage alpha 3, phage WA13, etc.; phage G4; phage phiX174 and related coliphages. Many additional phages known to those of skill in the art remain unclassified. The sequence of many coat proteins are publicly available.

The nucleic acid sequence encoding the viral capsid or proteins can be modified to alter the formation of VLPs (see e.g. Brumfield, et al. (2004) *J. Gen. Virol.* 85: 1049-1053). For example, three general classes of modification are most typically generated for modifying VLP expression and assembly.

These modifications are designed to alter the interior, exterior or the interface between adjacent subunits in the assembled protein cage. To accomplish this, mutagenic primers can be used to: (i) alter the interior surface charge of the viral nucleic acid binding region by replacing basic residues (e.g. K, R) in the N terminus with acidic glutamic acids (Douglas et al., 2002b); (ii) delete interior residues from the N terminus (in CCMV, usually residues 4-37); (iii) insert a cDNA encoding an 11 amino acid peptide cell-targeting sequence (Graf et al., 1987) into a surface exposed loop and (iv) modify interactions between viral subunits by altering the metal binding sites (in CCMV, residues 81/148 mutant).

Nonnatural Amino Acids.

Examples of nonnatural amino acids that can be used in the methods of the invention include: an nonnatural analogue of a tyrosine amino acid; an nonnatural analogue of a glutamine amino acid; an nonnatural analogue of a phenylalanine amino acid; an nonnatural analogue of a serine amino acid; an nonnatural analogue of a threonine amino acid; an nonnatural analogue of a pyrrolysine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; a metal-containing amino acid; a radioactive amino acid; a photocaged and/or photoisomerizable amino acid; a biotin or biotin-analogue containing amino acid; a glycosylated or carbohydrate modified amino acid; a keto containing amino acid; amino acids comprising polyethylene glycol or polyether; a heavy atom substituted amino acid; a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a redox-active amino acid; an α-hydroxy containing acid; an amino thio acid containing amino acid; an α,α disubstituted amino acid; a β-amino acid; a cyclic amino acid other than proline, etc.

Nonnatural amino acids of interest for the purpose of this invention may be selected to provide a reactant group for CLICK chemistry reactions (see *Click Chemistry: Diverse Chemical Function from a Few Good Reactions* Hartmuth C. Kolb, M. G. Finn, K. Barry Sharpless Angewandte Chemie International Edition Volume 40, 2001, P. 2004, herein specifically incorporated by reference), or for other bioorthogonal reactions. For example, the amino acids p-acetyl-L-phenylalanine, p-azido-L-phenylalanine and p-propargyloxy-L-phenylalanine (pPaF) are of interest for this purpose.

Other bioorthogonal chemistries such as the copper-free variant of this reaction (which uses a strained alkyne moiety), oxime formation between an acetyl group and an amino-oxy moiety, and a modified Staudinger ligation between an azide and a phosphine are also of interest. Of these bioorthogonal chemistries, only the copper-free variant of the azide-alkyne cycloaddition can be used to polymerize proteins directly using nnAAs that are pyrrolysine analogs instead of tyrosine analogs. The other bioorthogonal chemistries require the use of bi- or multi-functional small molecule linkers since only one of the two moieties can be incorporated into a protein as part of a nnAA. For example, proteins with multiple copies of p-acetyl-Phe can be polymerized using oxime formation only if they are connected via small molecule linkers that have terminal amino-oxy moieties.

Orthogonal Components.

As used herein, orthogonal components include a tRNA aminoacylated with an nonnatural amino acid, where the orthogonal tRNA base pairs with a codon that is not associated with another amino acid, e.g. a stop codon; a 4 bp codon, methionine replacement, etc. The reaction mixture may further comprise a tRNA synthetase capable of aminoacylating (with an nonnatural amino acid) the cognate orthogonal tRNA. Such components are known in the art, for example as described in U.S. Pat. No. 7,045,337, issued May 16, 2006. The orthogonal tRNA recognizes a selector codon, which may be nonsense codons, such as, stop codons, e.g., amber, ochre, and opal codons; four or more base codons; codons derived from natural or nonnatural base pairs and the like. The orthogonal tRNA anticodon loop recognizes the selector codon on the mRNA and incorporates the nonnatural amino acid at this site in the polypeptide.

Orthogonal tRNA synthetase is preferably synthesized exogenously, purified and added to the reaction mix of the invention, usually in a defined quantity, of at least about 10 µg/ml, at least about 20 µg/ml, at least about 30 µg/ml, and not more than about 200 µg/ml. The protein may be synthesized in bacterial or eukaryotic cells and purified, e.g. by affinity chromatography, PAGE, gel exclusion chromatography, reverse phase chromatography, and the like, as known in the art.

The orthogonal tRNA may be synthesized in the cells from which the extract for cell-free synthesis is obtained; may be exogenously synthesized, purified and added to the reaction mix, or may be synthesized de novo, where the cell-free synthesis reaction allows for transcription and translation reactions. Where the orthogonal tRNA is synthesized in the cells from which the extract for cell-free synthesis is obtained, the expression may be controlled through appropriate selection of promoters, medium, and the like.

In vitro synthesis, as used herein, refers to the cell-free synthesis of polypeptides in a reaction mix comprising biological extracts and/or defined reagents. The reaction mix will comprise a template for production of the macromolecule, e.g. DNA, mRNA, etc.; monomers for the macromolecule to be synthesized, e.g. amino acids, nucleotides, etc., and such co-factors, enzymes and other reagents that are necessary for the synthesis, e.g. ribosomes, tRNA, polymerases, transcriptional factors, etc. Such synthetic reaction systems are well-known in the art, and have been described in the literature. The cell free synthesis reaction may be performed as batch, continuous flow, or semi-continuous flow, as known in the art.

In some embodiments of the invention, cell free synthesis is performed in a reaction where oxidative phosphorylation is activated, e.g. the CYTOMIM™ system. The activation of the respiratory chain and oxidative phosphorylation is evidenced by an increase of polypeptide synthesis in the presence of $O_2$. In reactions where oxidative phosphorylation is activated, the overall polypeptide synthesis in presence of $O_2$ is reduced by at least about 40% in the presence of a specific electron transport chain inhibitor, such as HQNO, or in the absence of $O_2$. The reaction chemistry may be as described in international patent application WO 2004/016778, herein incorporated by reference.

The CYTOMIM™ environment for synthesis utilizes cell extracts derived from bacterial cells grown in medium containing glucose and phosphate, where the glucose is present initially at a concentration of at least about 0.25% (weight/volume), more usually at least about 1%; and usually not more than about 4%, more usually not more than about 2%. An example of such media is 2YTPG medium, however one of skill in the art will appreciate that many culture media can be adapted for this purpose, as there are many published media suitable for the growth of bacteria such as *E. coli*, using both defined and undefined sources of nutrients (see Sambrook, J., E. F. Fritsch, and T. Maniatis. 1989. Molecular Cloning: A Laboratory Manual, $2^{nd}$ edition. Cold Spring Harbor University Press, Cold Spring Harbor, N.Y. for examples of glucose containing media). Alternatively, the culture may be grown using a protocol in which the glucose is continually fed as required to maintain a high growth rate in either a defined or complex growth medium.

The reaction mixture may be supplemented by the inclusion of vesicles, e.g. an inner membrane vesicle solution. Where provided, such vesicles may comprise from about 0 to about 0.5 volumes, usually from about 0.1 to about 0.4 volumes.

In some embodiments, PEG will be present in not more than trace amounts, for example less than 0.1%, and may be less than 0.01%. Reactions that are substantially free of PEG contain sufficiently low levels of PEG that, for example, oxidative phosphorylation is not PEG-inhibited. The molecules spermidine and putrescine may be used in the place of PEG. Spermine or spermidine is present at a concentration of at least about 0.5 mM, usually at least about 1 mM, preferably about 1.5 mM, and not more than about 2.5 mM. Putrescine is present at a concentration of at least about 0.5 mM, preferably at least about 1 mM, preferably about 1.5 mM, and not more than about 2.5 mM. The spermidine and/or putrescine may be present in the initial cell extract or may be separately added.

The concentration of magnesium in the reaction mixture affects the overall synthesis. Often there is magnesium present in the cell extracts, which may then be adjusted with additional magnesium to optimize the concentration. Sources of magnesium salts useful in such methods are known in the art. In one embodiment of the invention, the source of magnesium is magnesium glutamate. A preferred concentration of magnesium is at least about 5 mM, usually at least about 10 mM, and preferably a least about 12 mM; and at a concentration of not more than about 25 mM, usually not more than about 20 mM. Other changes that may enhance synthesis or reduce cost include the omission of HEPES buffer and phosphoenol pyruvate from the reaction mixture.

The system can be run under aerobic and anaerobic conditions. Oxygen may be supplied, particularly for reactions larger than 15 µl, in order to increase synthesis yields. The headspace of the reaction chamber can be filled with oxygen; oxygen may be infused into the reaction mixture; etc. Oxygen can be supplied continuously or the headspace of the reaction chamber can be refilled during the course of protein expression for longer reaction times. Other electron acceptors, such as nitrate, sulfate, or fumarate may also be supplied in conjunction with preparing cell extracts so that the required enzymes are active in the cell extract.

It is not necessary to add exogenous cofactors for activation of oxidative phosphorylation. Compounds such as nicotinamide adenine dinucleotide (NADH), $NAD^+$, or acetyl-coenzyme A may be used to supplement protein synthesis yields but are not required. Addition of oxalic acid, a metabolic inhibitor of phosphoenolpyruvate synthetase (Pps), may be beneficial in increasing protein yields, but is not necessary.

The template for cell-free protein synthesis can be either mRNA or DNA, preferably a combined system continuously generates mRNA from a DNA template with a recognizable promoter. Either an endogenous RNA polymerase is used, or an exogenous phage RNA polymerase, typically T7 or SP6, is added directly to the reaction mixture. Alternatively, mRNA can be continually amplified by inserting the message into a template for QB replicase, an RNA dependent RNA polymerase. Purified mRNA is generally stabilized by chemical modification before it is added to the reaction mixture. Nucleases can be removed from extracts to help stabilize mRNA levels. The template can encode for any particular gene of interest.

Other salts, particularly those that are biologically relevant, such as manganese, may also be added. Potassium is generally present at a concentration of at least about 50 mM, and not more than about 250 mM. Ammonium may be present, usually at a concentration of not more than 200 mM, more usually at a concentration of not more than about 100 mM. Usually, the reaction is maintained in the range of about pH 5-10 and a temperature of about 20°-50° C.; more usually, in the range of about pH 6-9 and a temperature of about 25°-40° C. These ranges may be extended for specific conditions of interest.

Metabolic inhibitors to undesirable enzymatic activity may be added to the reaction mixture. Alternatively, enzymes or factors that are responsible for undesirable activity may be removed directly from the extract or the gene encoding the undesirable enzyme may be inactivated or deleted from the chromosome.

Biological Extracts.

For the purposes of this invention, biological extracts are any preparation comprising the components required for protein synthesis machinery, usually a bacterial cell extract, wherein such components are capable of expressing a nucleic acid encoding a desired protein. Thus, a bacterial extract comprises components that are capable of translating messenger ribonucleic acid (mRNA) encoding a desired protein, and optionally comprises components that are capable of transcribing DNA encoding a desired protein. Such components include, for example, DNA-directed RNA polymerase (RNA polymerase), any transcription activators that are required for initiation of transcription of DNA encoding the desired protein, transfer ribonucleic acids (tRNAs), aminoacyl-tRNA synthetases, 70S ribosomes, $N^{10}$-formyltetrahydrofolate, formylmethionine-tRNAf$^{Met}$ synthetase, peptidyl transferase, initiation factors such as IF-1, IF-2 and IF-3, elongation factors such as EF-Tu, EF-Ts, and EF-G, release factors such as RF-1, RF-2, and RF-3, and the like.

In a preferred embodiment of the invention, the reaction mixture comprises extracts from bacterial cells, e.g. *E. coli* S30 extracts, as is known in the art. In some embodiments the bacterial strain is modified such that it endogenously expresses an orthogonal tRNA. For convenience, the organism used as a source of extracts may be referred to as the source organism. Methods for producing active extracts are known in the art, for example they may be found in Pratt (1984), Coupled transcription-translation in prokaryotic cell-free systems, p. 179-209, in Hames, B. D. and Higgins, S. J. (ed.), Transcription and Translation: A Practical Approach, IRL Press, New York. Kudlicki et al. (1992) *Anal Biochem* 206(2):389-93 modify the S30 *E. coli* cell-free extract by collecting the ribosome fraction from the S30 by ultracentrifugation. Zawada and Swartz Biotechnol Bioeng, 2006. 94(4): p. 618-24 and Liu et al., 2005, Biotechnol Progr 21:460 teach a modified procedure for extract preparation.

The bacterial strain from which the extract is derived may be further modified for the purposes of the invention. In one embodiment, the extract is derived from an *E. coli* strain deficient in one or more proteins, e.g. strain KC6

(A19ΔtonAΔtnaAΔspeAΔendAΔsdaAΔsdaBΔgshA met⁺), KGK10 (A19ΔspeAΔtnaAΔtonAΔendAΔsdaAΔsdaBΔgshAΔgor met⁺ which can include TrxB-HA, ARG1 (A19ΔtonAΔtnaAΔspeAΔendAΔsdaAΔsdaBΔgshA met⁺ OmpTD83A), ARG2 (A19ΔspeAΔtnaAΔtonAΔendAΔsdaAΔsdaBΔgshAΔgor met⁺ OmpTD83A which can include TrxB-HA); MCJ29 (A19ΔspeAΔtnaAΔompTΔptrCΔdegPΔtonAΔendA met⁺) and the like.

Folding, as used herein, refers to the process of forming the three-dimensional structure of polypeptides and proteins, where interactions between amino acid residues act to stabilize the structure. Non-covalent interactions are important in determining structure, and the effect of membrane contacts with the protein may be important for the correct structure. For naturally occurring proteins and polypeptides or derivatives and variants thereof, the result of proper folding is typically the arrangement that results in optimal biological activity, and can conveniently be monitored by assays for activity, e.g. ligand binding, enzymatic activity, etc.

In some instances, for example where the desired product is of synthetic origin, assays based on biological activity will be less meaningful. The proper folding of such molecules may be determined on the basis of physical properties, energetic considerations, modeling studies, and the like.

The synthesis of membrane-associated protein may be followed by direct isolation of the active, membrane associated forms, i.e. in the absence of refolding or post-translational introduction of membranes. The separation procedure may utilize conditions that maintain membrane integrity, as is known in the art or may use any of several membrane active detergents used to isolated membrane proteins as commonly practiced in the art.

Separation procedures of interest include affinity chromatography. Affinity chromatography makes use of the highly specific binding sites usually present in biological macromolecules, separating molecules on their ability to bind a particular ligand. Covalent bonds attach the ligand to an insoluble, porous support medium in a manner that overtly presents the ligand to the protein sample, thereby using natural biospecific binding of one molecular species to separate and purify a second species from a mixture. Antibodies are commonly used in affinity chromatography. Preferably a microsphere or matrix is used as the support for affinity chromatography. Such supports are known in the art and are commercially available, and include activated supports that can be coupled to the linker molecules. For example, Affi-Gel supports, based on agarose or polyacrylamide are low pressure gels suitable for most laboratory-scale purifications with a peristaltic pump or gravity flow elution. Affi-Prep supports, based on a pressure-stable macroporous polymer, are suitable for preparative and process scale applications.

Proteins may also be separated by ion exchange chromatography, and/or concentrated, filtered, dialyzed, etc., using methods known in the art.

Enzyme Pathway: As used herein, the term "enzyme pathway" or "pathway of interest" refers to a system for converting a substrate to a product of interest, where the system comprises a plurality of enzymes and may additionally comprise substrates acted upon by one or more of the enzymes, products of the enzyme-catalyzed reaction, co-factors utilized by the enzymes, and the like. The system may be present in an intact cell, or in a lysate of a cell. Many metabolic pathways are known and have been described in microbial systems, and are accessible in public databases. For example, a number of reference books are available, including, inter alia, The Metabolic Pathway Engineering Handbook (2009), ed. C. Smolke, CRC, ISBN-10: 1420077651 and 1439802963; Metabolic Engineering: Principles and Methodologies (1998) Stephanopoulos, Academic Press ISBN-10: 0126662606, Greenberg D M. Metabolic Pathways: Energetics, tricarboxylic acid cycle, and carbohydrates. Academic Press; 1967; Greenberg M. Metabolic pathways. Academic Press; 1968; Greenberg D M. Metabolic pathways. Academic; 1970; and Greenberg D M, Vogel H J. Metabolic pathways. Academic; 1971, each herein specifically incorporated by reference.

Pathways of interest include, without limitation, pathways involved in carbohydrate, amino acid, nucleic acid, steroid, and fatty acid metabolism, and may include synthesis of antibiotics, e.g. actinomycin, bleomycin, rifamycin, chloramphenicol, tetracycline, lincomycin, erythromycin, streptomycin, cyclohexamide, puromycin, cycloserine, bacitracin, penicillin, cephalosporin, vancomycin, polymyxin, and gramicidin; biosurfactants e.g. rhamnolipids, sophorolipids, glycolipids, and lipopeptides; biological fuels e.g. bioethanol, biodiesel, and biobutanol; amino acids e.g. L-glutamate, L-lysine, L-phenylalanine, L-aspartic acid, L-isoleucine, L-valine, L-tryptophan, L-proline (hydroxyproline), L-threonine, L-methionine, and D-p-hydroxyphenylglycine; organic acids e.g. citric acid, lactic acid, gluconic acid, acetic acid, propionic acid, succinic acid, fumaric acid, and itaconic acid; fatty acids e.g. arachidonic acid, polyunsaturated fatty acid (PUBA), and .gamma.-linoleic acid; polyols e.g. glycerol, mannitol, erythritol, and xylitol; flavors and fragrances e.g. vanillin, benzaldehyde, dixydroxyacetone, 4-(R)-decanolide, and 2-actyl-1-pyrroline; nucleotides e.g. 5'-guanylic acid and 5'-inosinic acid; vitamins e.g. vitamin C, vitamin F, vitamin B2, provitamin D2, vitamin B12, folic acid, nicotinamide, biotin, 2-keto-L-gulonic acid, and provitamin Q10; pigments e.g. astaxathin, .beta.-carotene, leucopene, monascorubrin, and rubropunctatin; sugars and polysaccharides e.g. ribose, sorbose, xanthan, gellan, and dextran; biopolymers and plastics e.g. polyhydroxyalkanoates (PHA), poly-.gamma.-glutamic acid, and 1,3-propanediol; and the like as known in the art.

A number of reactions may be catalyzed by enzymes in pathways of interest. Broad classes, which can be identified by enzyme classification number, provided in parentheses, include (EC 1) oxidoreductases, e.g. dehydrogenases, oxidases, reductases, oxidoreductases, synthases, oxygenases, monooxygenases, dioxygenases, lipoxygenases, hydrogenases, transhydrogenases, peroxidases, catalases, epoxidases, hydroxylases, demethylases, desaturases, dismutases, hydroxyltransferases, dehalogenases, deiodinases, etc.; (EC2) transferases, e.g. Transaminases, kinases, dikinases, methyltransferases, hydroxymethyltransferases, formyltransferases, formiminotransferases, carboxytransferases, carbamoyltransferases, amidinotransferases, transaldolases, transketolases, acetyltransferases, acyltransferases palmitoyltransferases, succinyltransferases, malonyltransferases, galloyltransferases, sinapoyltransferases, tigloyltransferases, tetradecanoyltransferases, hydroxycinnamoyltransferases, feruloyltransferases, mycolyltransferases, benzoyltransferases, piperoyltransferases, trimethyltridecanoyltransferase, myristoyltransferases, coumaroyltransferases, thiolases, aminoacyltransferases, phosphorylases, hexosyltransferases, pentosyltransferases, sialyltransferases, pyridinylases, diphosphorylases, cyclotransferases, sulfurylases, adenosyltransferases, carboxyvinyltransferases, isopentenyltransferases, aminocarboxypropyltransferases, dimethylallyltransferases, farnesyltranstransferases, hexaprenyltranstransferases, decaprenylcistransferases, pentaprenyltranstransferases, nonaprenyltransferases, geranylgeranyltransferases, aminocarboxypropyltransferases, oximinotransferases, purinetransferases, phosphodismutases, phosphotransferases, nucleotidyltransferases, polymerases, cholinephosphotransferases, phosphorylmutases, sulfurtransferases, sulfotransferases, CoA-transferases, etc.; (EC3) hydrolases, e.g. lipases, esterases, amylases, peptidases, hydrolases, lactonases, deacylases, deacetylases, pheophorbidases, depolymerases, thiolesterases, phosphatases, diphosphatases, triphosphatases, nucleotidases, phytases, phosphodiesterases, phospholipases, sulfatases, cyclases, oligonucleotidases, ribonucleases, exonucleases, endonucleases, glycosidases, nucleosidases, glycosylases, aminopeptidases, dipeptidases, carboxypeptidases, metallocarboxypeptidases, omega-peptidases, serine endopeptidases, cystein endopeptidases, aspartic endopeptidases, metalloendopeptidases, threonine endopeptidases, aminases, amidases, desuccinylases, deformylases, acylases, deiminases, deaminases, dihydrolases, cyclohydrolases, nitrilases, ATPases, GTPases, halidases, dehalogenases, sulfohydrolases, etc.; (EC 4) lyases, e.g. decarboxylases, carboxylases, carboxykinases, aldolases, epoxylyases, oxoacid-lyases, carbon-carbon lyases, dehydratases, hydratases, synthases, endolyases, exolyases, ammonia-lyases, amidine-lyases, amine-lyases, carbon-sulfur lyases, carbon-halide lyases, phosphorus-oxygen lyases, dehydrochlorinases, etc.; (EC 5) isomerases, e.g. isomerases, racemases, mutases, tautomerases, phosphomutases, phosphoglucomutases, aminomutases, cycloisomerase, cyclases, topoisomerases, etc.; and (EC 6) ligases, e.g. synthetases, tNRA-ligases, acid-thiol ligases, amide synthases, peptide synthases, cycloligases, carboxylases, DNA-ligases, RNA-ligases, cyclases, etc.

Enzymes involved in a pathway may be classified according to the role of the enzymes. Direct involvement enzymes catalyze a reaction in the pathway. It is typical of pathways that such direct enzymes are one of a chain, where a product of a first enzyme is the substrate of a second, etc., which eventually results in the product of interest. Indirect involvement enzymes react in an associated pathway, usually in the production of a substrate used in the pathway.

Within a pathway, enzymes will vary in turnover rate and the effectiveness with which a product is produced. As a result, certain enzymes in a pathway become rate-limiting. Increasing the concentration of rate-limiting enzymes in a pathway (relative to non-rate limiting enzymes) allows increased flux through the pathway of interest.

A third class of enzymes are competing enzymes, which utilize a substrate or product of the pathway of interest. A characteristic of a competing enzyme is that the kinetics of the substrate conversion are sufficiently high that the presence of the enzyme decreases the overall yield and/or the rate of production of the desired final product catalyzed by the pathway of interest.

Enzymes in a pathway may be naturally occurring, or modified to optimize a characteristic of interest, e.g. substrate specificity, reaction kinetics, solubility, codon usage, etc. In some embodiments the complete pathway comprises enzymes from a single organism, however such is not required, and combining enzymes from multiple organisms is contemplated.

Methods for Synthesis and Conjugation

The reactions may utilize a large scale reactor, small scale, or may be multiplexed to perform a plurality of simultaneous syntheses. Continuous reactions will use a feed mechanism to introduce a flow of reagents, and may isolate the end-product as part of the process. Batch systems are also of interest, where additional reagents may be introduced to prolong the period of time for active synthesis. A reactor may be run in any mode such as batch, extended batch, semi-batch, semi-continuous, fed-batch and continuous, and which will be selected in accordance with the application purpose.

Strategies for synthesis where at least one nonnatural amino acid is introduced into the polypeptide strand during elongation include but are not limited to: (I) addition of exogenous purified orthogonal synthetase, nonnatural amino acid, and orthogonal tRNA to the cell-free reaction, (II) addition of exogenous purified orthogonal synthetase and nonnatural amino acid to the reaction mixture, but with orthogonal tRNA transcribed during the cell-free reaction, (III) addition of exogenous purified orthogonal synthetase and nonnatural amino acid to the reaction mixture, but with orthogonal tRNA synthesized by the cell extract source organism. Preferably the orthogonal components are driven by regulatable promoters, so that synthesis levels can be controlled although other measures may be used such as controlling the level of the relevant DNA templates by addition or specific digestion.

In order to prevent degradation of the orthogonal synthetase, the bacterial strain used to produce extracts may have a deleted or mutated ompT (outer membrane protein T). Where ompT is mutated, it is preferably mutated in such a way that the protease function is inactive, but the chaperone function is still present. Such extracts have decreased levels of synthetase degradation relative to an extract without such a mutation or deletion.

The reaction mixture may also be modified to maintain an oxidizing protein folding environment, for example by supplementing the reaction mix with GSSG at a concentration of from about 0.5 mM to about 10 mM, usually from about 1 mM to about 4 mM; supplementing with GSH at a concentration of from about 0.5 mM to about 10 mM, usually from about 1 mM to about 4 mM. Protein components such as 100 µg/mL DsbC or Skp may also be included. Cell extracts are optionally pretreated with iodoacetamide (IAM).

The reactions may be of any volume, either in a small scale, usually at least about 1 µl and not more than about 15 µl, or in a scaled up reaction, where the reaction volume is at least about 15 µl, usually at least about 50 µl, more usually at least about 100 µl, and may be 500 µl, 1000 µl, or greater. In most cases, individual reactions will not be more than about 10 ml, although multiple reactions can be run in parallel. However, in principle, reactions may be conducted at any scale as long as sufficient oxygen (or other electron acceptor) is supplied when needed.

In addition to the above components such as cell-free extract, genetic template, and amino acids, materials specifically required for protein synthesis may be added to the reaction. These materials include salts, folinic acid, cyclic AMP, inhibitors for protein or nucleic acid degrading enzymes, inhibitors or regulators of protein synthesis, adjusters of oxidation/reduction potential(s), non-denaturing surfactants, buffer components, spermine, spermidine, putrescine, etc.

The salts preferably include potassium, magnesium, and ammonium salts (e.g. of acetic acid or glutamic acid). One or more of such salts may have an alternative amino acid as a counter anion. There is an interdependence among ionic species for optimal concentration. These ionic species are typically optimized with regard to protein production. When changing the concentration of a particular component of the reaction medium, that of another component may be changed accordingly. For example, the concentrations of several components such as nucleotides and energy source compounds may be simultaneously adjusted in accordance with the change in those of other components. Also, the concentration levels of components in the reactor may be varied over time. The adjuster of oxidation/reduction potential may be dithiothreitol, ascorbic acid, glutathione and/or their oxidized forms.

In a semi-continuous operation mode, the outside or outer surface of the membrane is put into contact with predetermined solutions that are cyclically changed in a predetermined order. These solutions contain substrates such as amino acids and nucleotides. At this time, the reactor is operated in dialysis, diafiltration batch or fed-batch mode. A feed solution may be supplied to the reactor through the same membrane or a separate injection unit. Synthesized protein is accumulated in the reactor, and then is isolated and purified according to the usual method for protein purification after completion of the system operation. Vesicles containing the product may also be continuously isolated, for example by affinity adsorption from the reaction mixture either in situ or in a circulation loop as the reaction fluid is pumped past the adsorption matrix.

Where there is a flow of reagents, the direction of liquid flow can be perpendicular and/or tangential to a membrane. Tangential flow is effective for recycling ATP and for preventing membrane plugging and may be superimposed on perpendicular flow. Flow perpendicular to the membrane may be caused or effected by a positive pressure pump or a vacuum suction pump or by applying transmembrane pressure using other methods known in the art. The solution in contact with the outside surface of the membrane may be cyclically changed, and may be in a steady tangential flow with respect to the membrane. The reactor may be stirred internally or externally by proper agitation means.

During protein synthesis in the reactor, the protein isolating means for selectively isolating the desired protein may include a unit packed with particles coated with antibody molecules or other molecules for adsorbing the synthesized, desired protein. Preferably, the protein isolating means comprises two columns for alternating use.

The amount of protein produced in a translation reaction can be measured in various fashions. One method relies on the availability of an assay which measures the activity of the particular protein being translated. An example of an assay for measuring protein activity is a luciferase assay system, or chloramphenicol acetyl transferase assay system. These assays measure the amount of functionally active protein produced from the translation reaction. Activity assays will not measure full length protein that is inactive due to improper protein folding or lack of other post translational modifications necessary for protein activity.

Another method of measuring the amount of protein produced in coupled in vitro transcription and translation reactions is to perform the reactions using a known quantity of radiolabeled amino acid such as $^{35}$S-methionine, $^{3}$H-leucine or $^{14}$C-leucine and subsequently measuring the amount of radiolabeled amino acid incorporated into the newly translated protein. Incorporation assays will measure the amount of radiolabeled amino acids in all proteins produced in an in vitro translation reaction including truncated protein products. The radiolabeled protein may be further separated on a protein gel, and by autoradiography confirmed that the product is the proper size and that secondary protein products have not been produced.

The bioorthogonal azide-alkyne conjugation reactions will include a Cu(I) catalyst. This catalyst may be introduced directly to the reaction (e.g. in the form explained in the examples, the tetrakis complex) or may be added as a Cu(II) salt in conjunction with a reducing agent such as ascorbic acid. The reaction may be performed under anaerobic conditions (e.g. in an anaerobic glove box) or under aerobic conditions, but a reducing agent such as ascorbic acid is necessary to keep the Cu(I) reduced under aerobic conditions. In the case of conjugating polypeptides with disulfide bonds, conducting the reactions under anaerobic conditions may be preferred, since the reducing agent may also denature the disulfide-bonded polypeptide. The reaction may be performed at temperatures between 4 and 37 degrees, more typically at 25 degrees; the polypeptides may denature at higher temperatures. Ligands such as TTMA may be added to increase the efficiency of the conjugation reactions.

The stoichiometry of the conjugation reaction will be selected based on the desired target. In the simplest polymers, two polypeptides are synthesized where each has a single nonnatural amino acid, where the nonnatural amino acids are reactive with each other. The polypeptides may be combined in a roughly 1:1 molar ratio, under conjugation conditions, to produce covalently bound dimers, AB. Alternatively, one or more polypeptides may comprise two different and reactive nonnatural amino acids, to produce linear polymers: $AAAAA_n$, $BBBBB_n$, $ABABABABAB_n$.

Alternatively one polypeptide may have two nonnatural amino acids, such that the polypeptides are combined in a roughly 1:2 ratio, forming a trimer $AB_2$. The number of branches in such an arrangement can be modified as desired, e.g. a 1:3 ratio to form a tetramer $AB_3$, and so on.

A single base protein, including without limitation structural proteins such as collagens, fibrin, and the like, can be modified to comprise a plurality of nonnatural amino acids, to which multiple different proteins are linked, for example in a reaction mix of about 1:1:1:1 ratio to produce ABCD product.

The polymers produced by the methods of the invention are readily purified from the subunit monomers by any convenient method, e.g. affinity chromatography, size exclusion columns, etc.

Kits for the practice of the subject methods may also be provided. Such kits may include bacterial extracts for protein synthesis and site directed insertion of nonnatural amino acids, e.g. containing orthogonal tRNA and/or tRNA synthetase or polynucleotides encoding the same, buffers appropriate for reactions where oxidative phosphorylation is activated, and vesicles.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

Super-folder green fluorescent protein (sfGFP) was produced that contained multiple copies of either the nonnatural amino acid pAzF or pPaF. These modified proteins were then purified and reacted in the presence of a copper(I) catalyst and the tris(triazolylmethyl)amine (TTMA) ligand to create sfGFP polymers. We also measured the fluorescence of these proteins before and after the reaction, and have shown that the proteins retain fluorescence after polymerization.

Example 1

Incorporation of Multiple Copies of pAzF and pPaF into Proteins

Preparation of linearized o-tRNA plasmid: The plasmid encoding the ribozyme-tRNA construct, pY71HHotDNA, was transformed into DH5α cells. The transformed cells were grown in 1 L cultures using Terrific Broth (Invitrogen), and the plasmid was subsequently purified using MaxiPrep columns (Qiagen) according to the manufacturer's protocol.

1-2 mg of the plasmid was digested with the restriction enzyme BstNI (New England Biolabs) at 60° C. for 2.5 hours. The digested plasmid was ethanol-precipitated, centrifuged and the pellet resuspended in 10 mM Bis-Tris buffer at pH 7.4. The concentration of the resuspended linearized plasmid was measured by absorbance at 260 nm.

Preparation of the aminoacyl-tRNA synthetase enzyme specific to pPaF (pPaFRS) or pAzF (pAzFRS): The gene encoding pPaFRS was ligated into the pY71 vector with a C-terminal $His_6$-tag, and BL21(DE3) pLysS cells were transformed with the resultant vector. These cells were grown in 1 L shake flasks at 37° C. for 12 hours. When the cell cultures reached an optical density (measured at 600 nm) of 0.6, 1 mM isopropyl β-D-1-thiogalactopyranoside (IPTG) was added to the culture medium to start protein synthesis. The cells were lysed using the BugBuster Master Mix reagent (Novagen) according to the manufacturer's protocol, and the protein was purified via immobilized metal affinity chromatography using a 1-mL HisTrap HP column (GE Healthcare). Fractions containing pPaFRS were dialyzed overnight into 10 mM phosphate, 20% w/v sucrose at pH 7.5.

The gene encoding the pAzFRS enzyme was cloned into the pK7 vector with a C-terminal $His_6$-tag. The same protocol was followed to produce, purify, and formulate pAzFRS.

Cell-free protein synthesis (CFPS): The PANOx-SP cell-free system was used to incorporate one or multiple copies (up to six) of either pAzF or pPaF into sfGFP at the following positions: 23, 39, 52, 66, 74, 92, 106, 117, 143, 151, 182, 189, 200, 212 and 223. 25 μl or 3 ml cell-free reaction mixtures included: 20 mM magnesium glutamate, 10 mM ammonium glutamate, 175 mM potassium glutamate, 1.2 mM ATP, 0.86 mM each of CMP, GMP and UMP, 10 mM potassium phosphate, 34 μg/mL folinic acid, 170.9 μg/mL E. coli tRNAs, 33 mM phosphoenolpyruvate (PEP), 1.5 mM spermidine, 1 mM putrescine, 0.33 mM NAD, 0.27 mM coenzyme A, 2.7 mM sodium oxalate, 2 mM each of the 20 unlabeled amino acids, 5 μM L-[U-$^{14}$C]-leucine, 100 μg/mL T7 RNAP, either 2 mM pAzF or 4 mM pPaF, either 0.3 mg/mL pAzFRS or 0.5 mg/mL pPaFRS, either 0.2 mg/mL of the linearized o-tRNA plasmid or 20-40 μg/mL of the o-tRNA template synthesized using PCR$^3$, 6 nM plasmid encoding the sfGFP construct with a C-terminal Strep-tag, and 0.24 volume of E. coli S30 extract prepared from the KC6 strain as described previously. The cell-free reaction solutions were incubated at 30° C. for 16 hours, and the full-length, soluble modified protein yields were measured via scintillation counting and densitometry.

Figure 3:
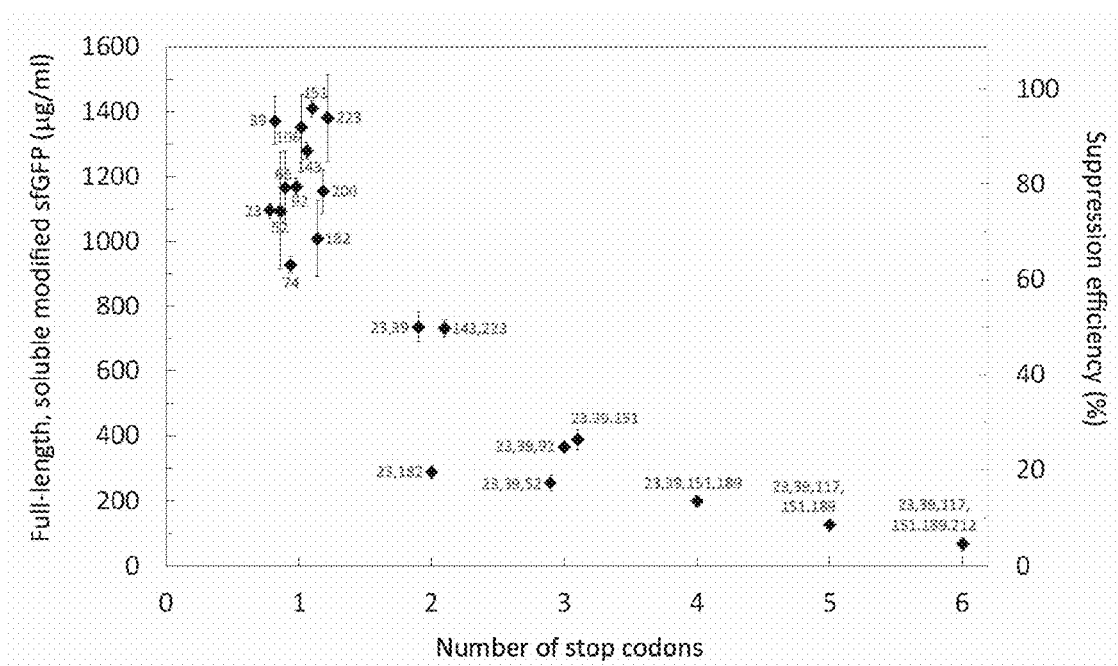
FIG. 3: Full-length and soluble sfGFP yields containing one to six copies of the tyrosine analog pPaF. The numbers indicate the site of nnAA substitution along the primary sequence. Suppression efficiency is defined as the ratio of yields of proteins containing nnAAs over the yield of the natural protein. Error bars indicate ±1 standard deviation for 3 reactions.

Results: The yields of modified sfGFP containing one to six copies of pPaF are given in FIG. 3; full-length, soluble yields of sfGFP containing one pPaF. Similar yields were obtained when pAzF was incorporated into sfGFP instead of pPaF. CFPS was previously used to modify proteins with one copy of either pAzF or pPaF, but these data represent the first demonstration of cell-free production of modified proteins containing multiple copies of these nnAAs.

Example 2

Formation of Protein Polymers via Click Chemistry

Purification of modified proteins: Modified sfGFP proteins were purified using Strep-Tactin affinity chromatography (IBA) according to the manufacturer's protocol. Fractions containing modified sfGFP were dialyzed overnight into 10 mM phosphate, 20% w/v sucrose at pH 7.5.

Protein polymerization via Click chemistry: Modified sfGFP with one, two or three copies of pAzF and sfGFP with one, two or three copies of pPaF were added to a Click reaction solution, which also contained Cu(I) catalyst and the TTMA ligand. The Cu(I) catalyst, tetrakis(acetonitrile)copper(I) hexafluorophosphate ($[(CH_3CN)_4Cu]PF_6$), was purchased from Sigma. The solutions were incubated in an anaerobic glove box in the dark (to prevent the photodissociation of the aromatic azide) for 9 hours at room temperature.

Figure 4:
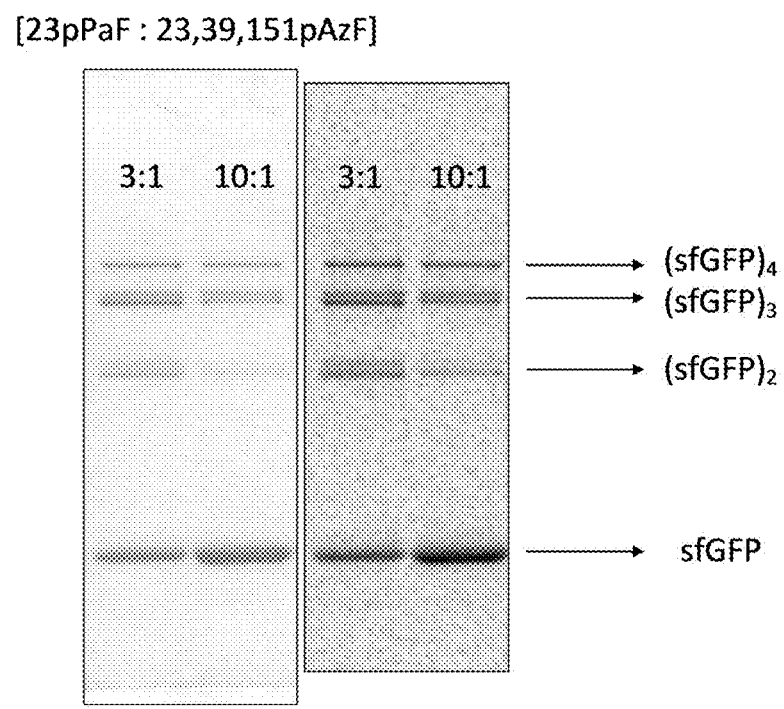
FIG. 4: The nnAA substitution sites 23, 39 and 151 are accessible to post-translational modification via Click chemistry. Modified sfGFP containing pPaF at position 23 (sfGFP23pPaF) was coupled to modified sfGFP containing pAzFs at positions 23, 39 and 151 (sfGFP23,39,151pAzF). The numbers show the molar ratio of these two proteins in each reaction. In the "3:1" reaction, 7.9 µM sfGFP23pPaF was reacted with 2.6 µM sfGFP23,39,151pAzF. In the "10:1" reaction, 11.9 µM sfGFP23pPaF was coupled to 1.2 µM sfGFP23,39,151pAzF. These reactions also contained 0.25 mM of Cu(I) catalyst and TTMA ligand. All of the proteins were labeled with $^{14}$C-leucine. The left panel shows Coomassie-stained sfGFP bands, while the right panel depicts the SDS-PAGE autoradiogram of radiolabeled sfGFPs.

Results: In the first set of reactions, the modified sfGFP with three pAzFs (sfGFP23,39,151pAzF) was coupled to sfGFP carrying one pPaF at position 23 (sfGFP23pPaF), to test the accessibility of the nnAA incorporation sites 23, 39 and 151. The individual reactions were labeled according to the molar ratio of sfGFP23pPaF to sfGFP23,39,151pAzF. The "3:1" reaction solution included 7.9 μM sfGFP23pPaF, 2.6 μM sfGFP23,39,151pAzF, 0.25 mM Cu(I) catalyst, and 0.25 mM TTMA. The "10:1" reaction solution contained 11.9 μM sfGFP23pPaF, 1.2 μM sfGFP23,39,151pAzF, 0.25 mM Cu(I) catalyst, and 0.25 mM TTMA. Dimers, trimers and tetramers of sfGFP were obtained after the Click reaction, thereby showing that these sites are accessible for covalent coupling with another macromolecule and that the proteins were connected to each other only through the nnAAs (FIG. 4). If the coupling reaction was not specific to the nnAAs, we would have observed sfGFP polymers larger than a tetramer.

Figure 5:
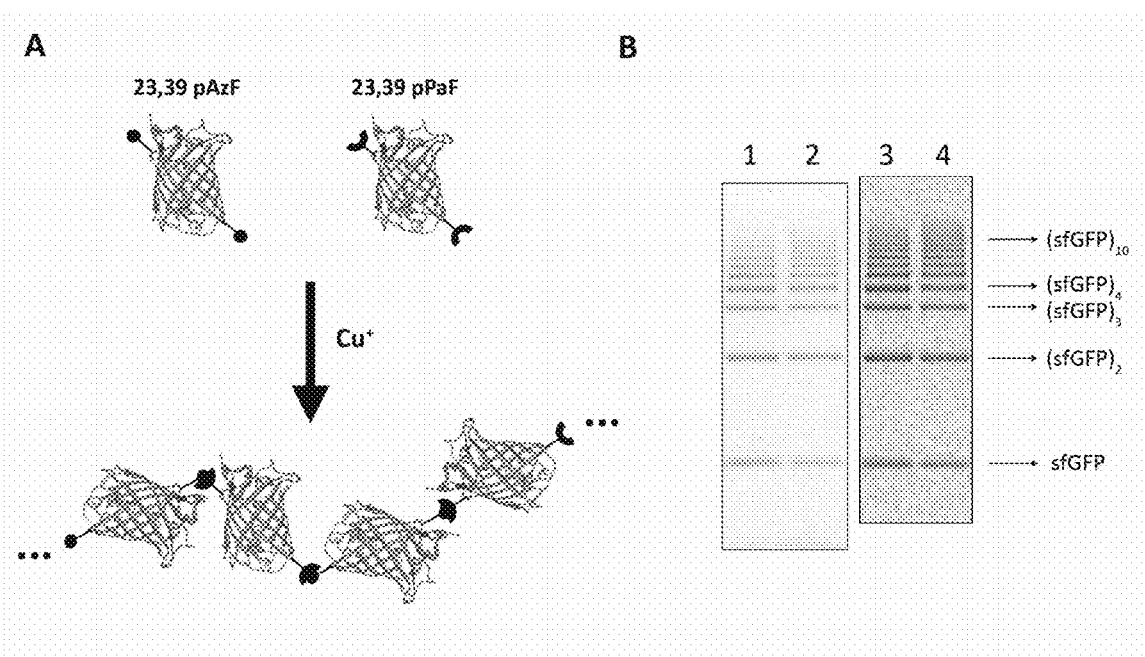
FIG. 5: Synthesis of linear sfGFP polymers. A) Cartoon showing the generation of a linear sfGFP polymer from directly coupling doubly-substituted sfGFPs using Click chemistry. B) Generation of a sfGFP ladder via direct polymerization of doubly-substituted sfGFP. Equimolar amounts of sfGFP containing two copies of pAzF or two copies of pPaF were reacted in an anaerobic glove box for 9 hours at room temperature. The numbers indicate the nnAA incorporation sites. The first reaction contained 6.5 µM sfGFP23,39pAzF, 6.5 µM sfGFP23,39pPaF, 0.25 mM Cu(I) catalyst, and 0.25 mM TTMA (Lanes 1 and 3). The second reaction contained 6.0 µM sfGFP23,39pAzF, 6.0 µM sfGFP23,39pPaF, 0.5 mM Cu(I) catalyst, and 0.5 mM TTMA (Lanes 2 and 4). The left panel (Lanes 1 and 2) shows the Coomassie-stained protein bands, and the right panel (Lanes 3 and 4) shows the autoradiogram of the SDS-PAGE gel.

In the second set of reactions, modified sfGFP with two copies of either pAzF or pPaF were covalently coupled to produce a mixture of linear sfGFP polymers (FIG. 5A). In these reactions, the sfGFP23,39pAzF and sfGFP23,39pPaF were added in equimolar concentrations. The reaction products were analyzed by SDS-PAGE and autoradiography (FIG. 5B). The first reaction contained 6.5 μM sfGFP23,39pAzF, 6.5 μM sfGFP23,39pPaF, 0.25 mM Cu(I) catalyst, and 0.25 mM TTMA (Lanes 1 and 3, FIG. 5B). The second reaction contained 6.0 μM sfGFP23,39pAzF, 6.0 μM sfGFP23,39pPaF, 0.5 mM Cu(I) catalyst, and 0.5 mM TTMA (Lanes 2 and 4, FIG. 5B). The polymers ranged from dimers to ones with more than 10 interconnected sfGFP protein molecules.

Figure 6:
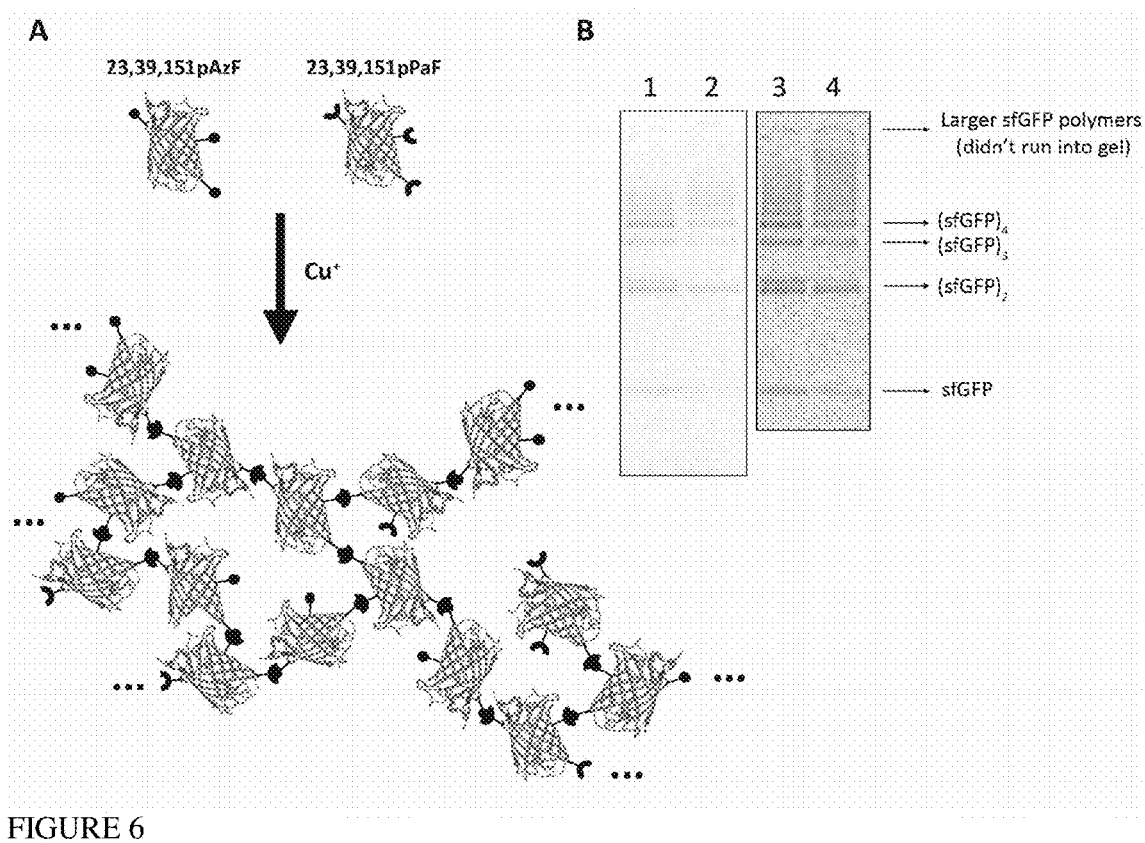
FIG. 6: Synthesis of branched sfGFP polymers. A) Cartoon showing the generation of a branched sfGFP polymer from directly coupling triply-substituted sfGFPs using Click chemistry. B) Larger branched sfGFP polymers were obtained when triply-substituted sfGFP proteins were covalently coupled. As seen more clearly on the right panel, some of the branched polymers were so large that they did not even run into the gel. Equimolar amounts of sfGFP containing three copies of pAzF or three copies of pPaF were reacted in an anaerobic glove box for 9 hours at room temperature. The numbers indicate the nnAA incorporation sites. The first reaction contained 2.9 µM sfGFP23,39,151pAzF, 2.9 µM sfGFP23,39,151pPaF, 0.25 mM Cu(I), and 0.25 mM TTMA (Lanes 1 and 3). The second reaction contained 2.7 µM sfGFP23,39,151pAzF, 2.7 µM sfGFP23,39,151pPaF, 0.5 mM Cu(I), and 0.5 mM TTMA (Lanes 2 and 4). The left panel (Lanes 1 and 2) shows the Coomassie-stained protein bands, and the right panel (Lanes 3 and 4) shows the autoradiogram of the SDS-PAGE gel.

In the third set of reactions, modified sfGFP with three copies of either pAzF or pPaF were coupled to produce branched sfGFP polymers (FIG. 6A); the sfGFP23,39, 151pAzF and sfGFP23,39,151pPaF were added in equimolar concentrations. The reaction products were again analyzed by SDS-PAGE and autoradiography (FIG. 6B). The first reaction contained 2.9 µM sfGFP23,39,151pAzF, 2.9 µM sfGFP23, 39,151pPaF, 0.25 mM Cu(I), and 0.25 mM TTMA (Lanes 1 and 3, FIG. 6B). The second reaction contained 2.7 µM sfGFP23,39,151pAzF, 2.7 µM sfGFP23,39,151pPaF, 0.5 mM Cu(I), and 0.5 mM TTMA (Lanes 2 and 4, FIG. 6B). Even though the concentrations of modified proteins were lower than in the second set of reactions, less unreacted monomeric sfGFP was observed in these reactions, probably because there were more conjugation sites per protein. In addition, larger sfGFP polymers were obtained when triply-substituted sfGFPs were coupled; some of the protein polymers were so large that they did not enter the 10% polyacrylamide gel (FIG. 6B). We were thus able to produce protein polymers in one step by conjugating proteins containing nnAAs at multiple sites using Click chemistry.

Example 3

Retention of Protein Activity in Linear Protein Polymers

Size exclusion chromatography (SEC) of Click reaction products: The doubly-substituted proteins (i.e. modified sfGFPs containing two copies of either pAzF or pPaF) were synthesized and purified as explained in Examples 1 and 2, respectively. Following purification, the proteins were concentrated using 10,000 MWCO centrifugal filter units (Millipore). The concentrated proteins were then coupled in a Click reaction solution containing 22.6 µM sfGFP23, 39pAzF, 22.6 µM sfGFP23,39pAzF, 0.5 mM TTMA and 1 mM Cu(I) catalyst. The reaction solution was incubated in an anaerobic glove box at room temperature for 12.5 hours. Following the incubation, the solution was desalted in the glove box into a deoxygenated SEC buffer that contained 10 mM potassium phosphate and 100 mM NaCl at pH 7.3 using a Microcon 3,000 MWCO centrifugal filter device (Millipore). The desalted solution containing the linear sfGFP polymers was then taken out of the glove box, and 72 µl was loaded onto an Ultrahydrogel 500 (10 µm, 7.8 mm×300 mm) size exclusion chromatography column (Waters). The sfGFP polymers were separated by running the SEC buffer at 0.3 ml/min through the column. 150 µl fractions were manually collected and each fraction was concentrated to 40 µl using a Microcon 3,000 MWCO centrifugal filter device.

Measurement of specific activity (fluorescence) and polymerization yield: Protein concentration and fluorescence of each fraction was measured, and the fluorescence was divided by the protein concentration to calculate the specific activity of the polymers in each fraction. The concentration of radiolabeled protein polymers was measured by scintillation counting and densitometry, and a 96-well plate fluorimeter (Berthold) was used to measure fluorescence.

The amount of each polymer in each fraction was estimated by densitometry, and these estimates were used to calculate the distribution of protein polymers after the reaction.

Figure 7:
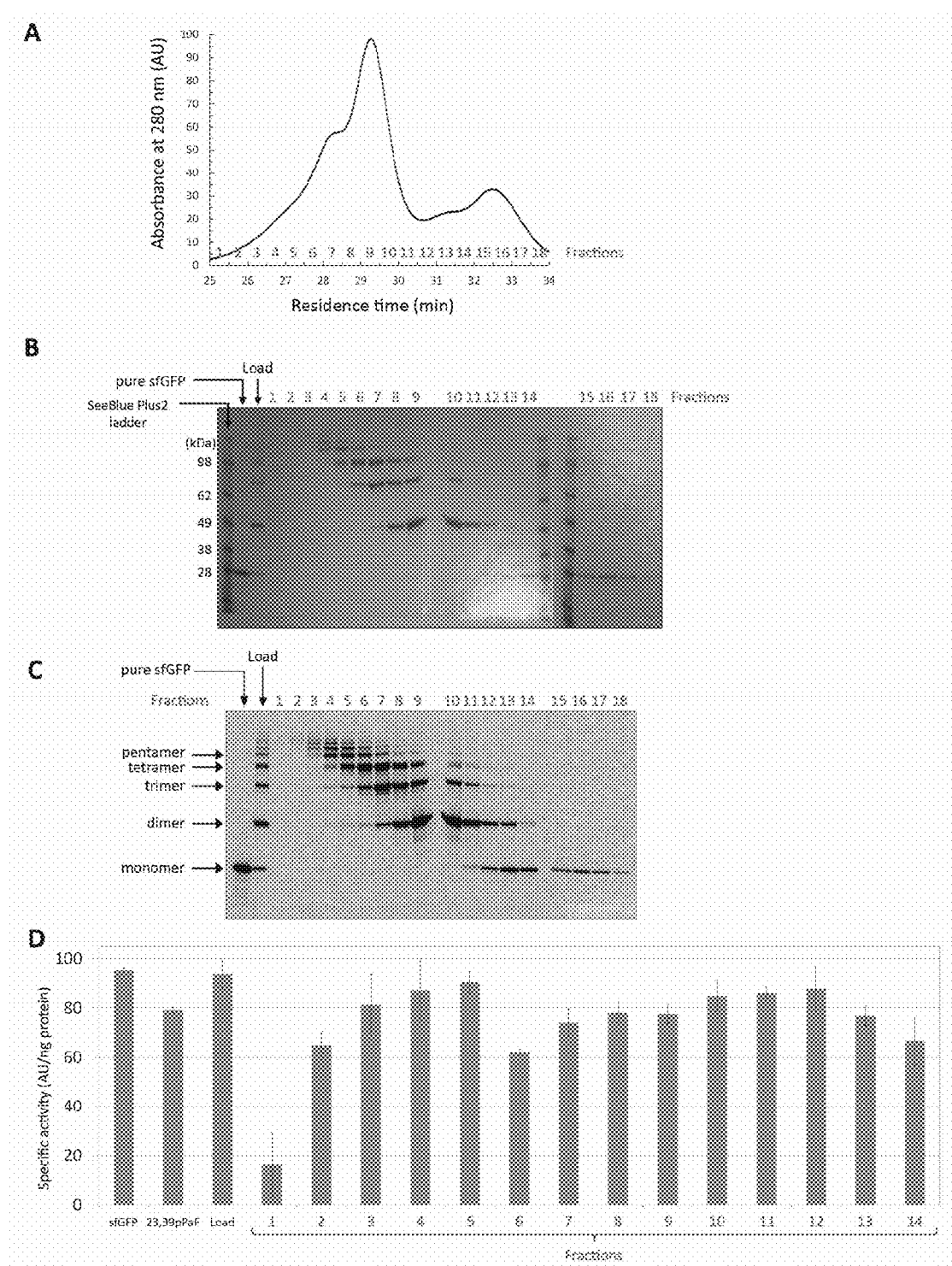
FIG. 7: Separation of linear sfGFP polymers using size exclusion chromatography (SEC). A) Absorbance at 280 nm shows presence of different polymers. After 7.5 ml, each fraction was manually collected for 0.5 min and contained 150 µl of protein solution. B) Coomassie-stained SDS-PAGE gel showing the contents of collected fractions. Purified monomeric sfGFP ("pure sfGFP") and the protein solution that was loaded onto the SEC column ("Load") were included for comparison. The protein ladder was also included to determine the weight and thus the polymerization state of each protein observed on the gel. C) Autoradiogram of the SDS-PAGE gels containing the different SEC fractions. The polymerization state of each band is indicated on the left. D) Specific activity of fractions 1-14 that contained either sfGFP polymers or a mixture of polymers and unreacted monomer. ≥78% of the specific sfGFP activity (i.e. fluorescence) was retained after polymerization. The first three bars indicate the specific activities of the purified natural sfGFP, the doubly-substituted sfGFP that contains pPaF at positions 23 and 39, and the protein mixture that was loaded onto the SEC column.

Results: A single SEC step was not sufficient to isolate individual sfGFP polymers, but was sufficient to separate the polymers away from unreacted sfGFP monomer. Fractions 1-10 contained the different sfGFP polymers, fractions 11-14 contained a mixture of polymers and unreacted monomer, while fractions 15-18 contained only the unreacted sfGFP monomer (FIGS. 7A, 7B and 7C). The sfGFP polymers in fractions 2-14 retained greater than or equal to 78% of the specific activity of sfGFP after the Click reaction (FIG. 7D). Finally, quantitative analysis of the reaction products shows that ~40% of the monomeric sfGFP was polymerized, ~40% assembled into dimers, ~15% was unreacted, and the remaining 5% was truncated. ~9% of monomeric sfGFP assembled into homopolymers with 5 or more monomers (Table 1).

TABLE 1

Distribution of sfGFP polymerization products from Example 3. Of the coupled sfGFP, dimeric sfGFP was the most abundant product (~40%), followed by sfGFP trimer (~18%), tetramer (~14%), etc (in order of increasing size). In addition, ~14% of the sfGFP monomer did not react and ~5% was degraded.

| Number of monomers | Fraction of total protein (%) |
|---|---|
| 9 | 0.3 |
| 8 | 0.5 |
| 7 | 1.1 |
| 6 | 2.5 |
| 5 | 4.6 |
| 4 | 13.7 |
| 3 | 18.3 |
| 2 | 40.4 |
| 1 | 14.1 |
| Degraded | 4.5 |

Example 4

Retention of Protein Activity in Branched Protein Polymers

Production and purification of modified proteins: 7.5 mL PANOx SP cell-free reaction solutions were incubated to produce the triply-substituted sfGFPs as explained in Example 1. These solutions contained 20 µg/mL of the o-tRNA template synthesized using PCR[3]. The triply-substituted sfGFPs were then purified using Strep-Tactin affinity chromatography (IBA) according to the manufacturer's protocol. Fractions containing modified sfGFP were dialyzed overnight into 10 mM phosphate at pH 7.5.

Size exclusion chromatography (SEC) of Click reaction products: After dialysis, the proteins were concentrated using 10,000 MWCO centrifugal filter units (Millipore). The concentrated proteins were coupled in a Click reaction solution containing 105 µM sfGFP23,39,151pAzF, 105 µM sfGFP23, 39,151pAzF, 0.5 mM TTMA and 1 mM Cu(I) catalyst. The reaction solution was incubated in an anaerobic glove box at room temperature for 13 hours. A second solution that contained 12 µM of each of the triply-substituted sfGFP and 0.5 mM TTMA but no Cu(I) catalyst was also incubated as a negative control. Following the incubation, the supernatant from the first reaction solution (that included all components of the Click reaction) was desalted in the glove box into a deoxygenated SEC buffer that contained 10 mM potassium phosphate and 100 mM NaCl at pH 7.3 using a Microcon 3,000 MWCO centrifugal filter device (Millipore). The desalted solution containing the branched sfGFP polymers was then taken out of the glove box, and 72 µl was loaded onto a Ultrahydrogel 500 (10 µm, 7.8 mm×300 mm) size exclusion chromatography column (Waters). The sfGFP polymers were separated by running the SEC buffer at 0.3 ml/min through the column. 150 µl fractions were manually collected and each fraction was concentrated to 40 µl using a Microcon 3,000 MWCO centrifugal filter device.

Separately, the fluorescent pellet that resulted from the Click reaction was washed 5 times with the deoxygenated SEC buffer. In each wash, 150 µl of buffer was added to the pellet, the suspension was centrifuged at 14,000 g for 15 min, and 150 µl of supernatant was taken out. These wash solutions were also concentrated to 40 µl using a Microcon 3,000 MWCO centrifugal filter device.

Measurement of specific activity (fluorescence) and polymerization yield: Protein concentration and fluorescence of each fraction and each wash solution was measured, and the fluorescence was divided by the protein concentration to calculate the specific activity of the polymers in each solution. The concentration of radiolabeled protein polymers was measured by scintillation counting and densitometry, and a 96-well plate Synergy fluorimeter (Biotek) was used to measure fluorescence.

Figure 8:
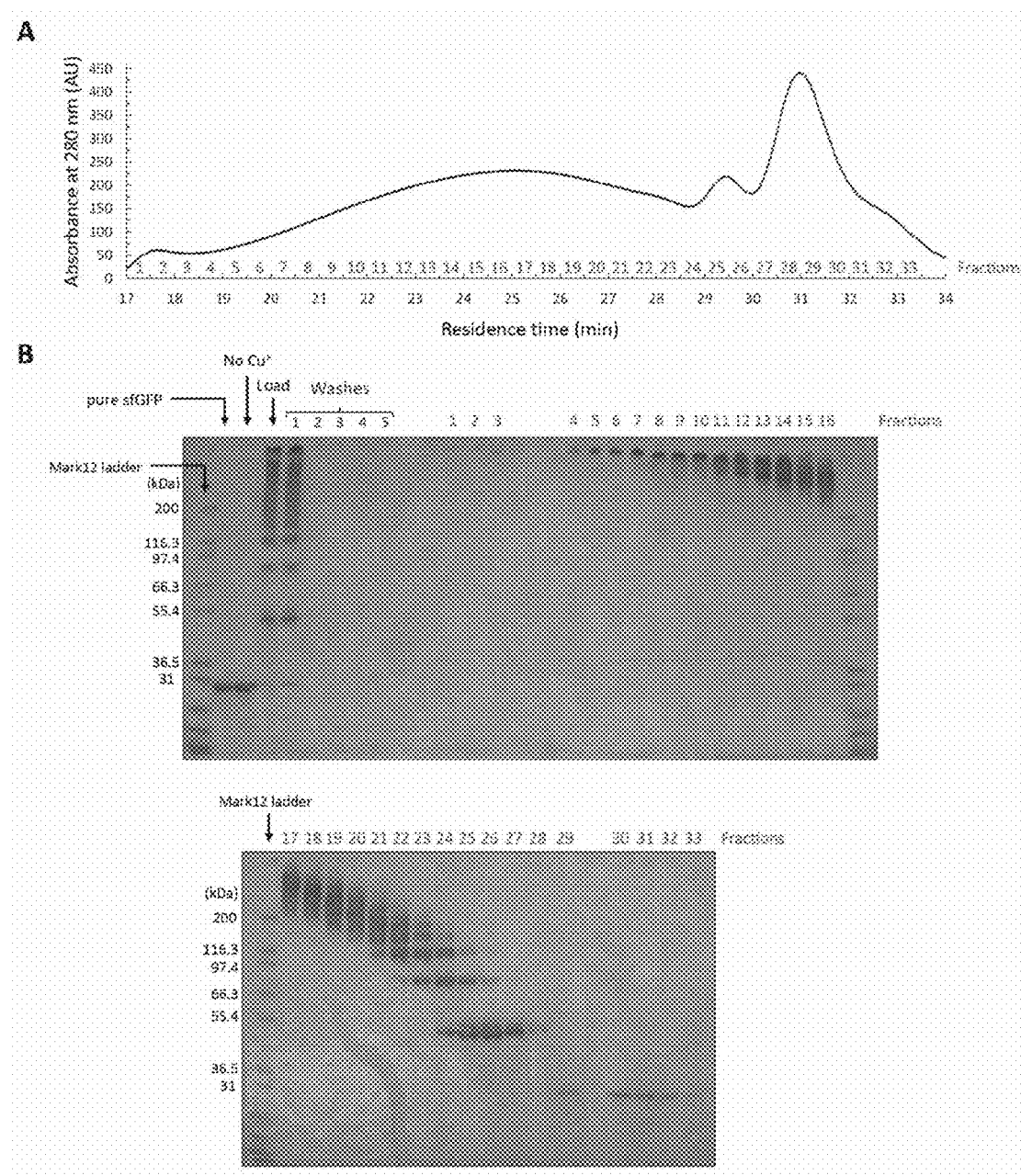
FIG. 8: Separation of branched sfGFP polymers using size exclusion chromatography (SEC). A) Absorbance at 280 nm shows presence of different polymers. After 5.1 ml, each fraction was manually collected for 0.5 min and contained 150 µl of protein solution. B) SDS-PAGE gels showing the contents of collected fractions. Purified monomeric sfGFP ("pure sfGFP"), the reaction solution with no Cu(I) catalyst (which served as negative control, "No Cu$^+$") and the protein solution that was loaded onto the SEC column ("Load") were included for comparison. The solutions obtained by washing the sfGFP pellet ("Washes 1-5") were also included. The Mark12 MW ladder was included to determine the polymerization state of the observed bands. C) Autoradiogram of the SDS-PAGE gels. The polymerization state of each band is indicated on the left. D) Specific activity of fractions 5-33 that contained either sfGFP polymers or the unreacted sfGFP monomer. ≥78% of the specific sfGFP activity (i.e. fluorescence) was retained after polymerization. The first four bars indicate the specific activities of the purified natural sfGFP, the triply-substituted sfGFP that contains pAzF at positions 23,39 and 151, the triply-substituted sfGFP that contains pPaF at the same positions, and the protein mixture that was loaded onto the SEC column. E) Photograph of the fluorescent sfGFP pellet that formed after the Click reaction in the microcentrifuge tube. The pellet was illuminated using a 302 nm UV transilluminator.

Results: Most of the sfGFP polymers (~70% of total protein) precipitated to form a pellet at the bottom of the reaction tube. A significant fraction (~14% of soluble sfGFP polymers, ~4% of total protein) of the soluble sfGFP polymers was so large that they did not run into the SDS-PAGE gel. Unreacted sfGFP monomers comprised only a tiny fraction (~0.7% of total protein) of the proteins. As observed in Example 3, a single SEC step was not sufficient to isolate individual sfGFP polymers, but was sufficient to separate the polymers away from unreacted sfGFP monomer. Fractions 1-28 contained the different sfGFP polymers, while fractions 29-33 contained only the unreacted sfGFP monomer (FIGS. 8A, 8B and 8C). As in Example 3, the sfGFP polymers (in fractions 5-28) retained greater than or equal to 78% of the specific activity of sfGFP after the Click reaction (FIG. 8D). The sfGFP pellet that was formed after Click reaction was also fluorescent (FIG. 8E), suggesting that this method can also be used to create biomaterials where the protein comprising the biomaterial retains its activity.

Example 5

Process Intensification by Covalent Coupling of Enzymes in a Conversion Pathway

The direct polymerization method outlined in Examples 1-4 can be used to covalently link enzymes that comprise a conversion pathway without the need for a separate organizing agent such as a scaffold or a solid matrix. When compared to a conventional enzymatic pathway, in which the enzymes diffuse freely in a solution, a polymer consisting of enzymes in a conversion pathway will increase the local concentration of enzymes and substrates, while decreasing the diffusion distance between the enzymes. As a result, when applied to the polymerization of enzymes in a pathway, this method would increase the efficiency of substrate conversion through the pathway and the productivity of the overall process. Furthermore, the enzymes would not necessarily need to be coupled in a particular order. Since each enzyme is evolved to be selective for its natural substrate, we can rely on the high selectivity of each enzyme for managing enzymatic fluxes.

Example 6

Selection of Sites for nnAA Incorporation

The following guidelines should be followed when choosing nnAA incorporation (i.e. attachment) sites for the construction of a 3-dimensional network of proteins: The sites need to be surface-exposed to minimize steric limitations and maximize attachment efficiency of the protein to other molecules. If the coupled protein is an enzyme, then the sites should be away from the active site so that covalent coupling of the enzyme does not perturb the active site, thereby reducing its activity after polymerization. If the crystal structures of the coupled enzymes are available, the attachment sites should be chosen such that the active sites of the enzymes are oriented toward each other to minimize substrate diffusion distances and maximize substrate conversion.

Example 7

Production of a Biomaterial with Integrated Folded Proteins

As demonstrated in Example 4 (FIG. 8E), the direct polymerization method can also be used to create biomaterials without the need for a scaffolding agent or a material such as PEG. These biomaterials can consist only of folded proteins such as the sfGFP pellet that we obtained (FIG. 8E), or of a mixture of folded proteins, structural proteins and small molecules. The proteins integrated into the biomaterial retain their activity when the biomaterial was synthesized using this method.

Example 8

Polymerization of Virus-Like Particles (VLPs)

Virus-like particles (VLPs) are non-infectious and have repetitive surfaces that can display molecules with a high surface density. They can serve as polyvalent scaffolds for the display of nucleic acids, proteins, and other chemical moieties. They can also be filled with cargo to serve as delivery vehicles. In addition, polymerization of VLPs can produce a novel biomaterial, which is light and flexible. For example VLPs internally reinforced with covalent bonds throughout the capsid and then joined with multiple covalent bonds would be exceptionally strong, thereby producing a highly useful material for fabrication and other purposes.

Cell-free protein synthesis (CFPS) is an effective method for producing VLPs composed of the Hepatitis B core protein (HBc), the MS2 bacteriophage coat protein, the Qβ bacteriophage coat protein (Bundy and Swartz, 2011), and other virus proteins. CFPS also provides a facile means for introducing non-natural amino acids (nnAAs) into VLPs, which allows for the direct VLP-VLP coupling using Cu(I)-catalyzed [3+2] cycloaddition click chemistry (Patel and Swartz, 2011). Furthermore, recent advances have demonstrated the introduction of disulfide bonds throughout the Hepatitis B core VLP to make it extremely stable.

Figure 9:
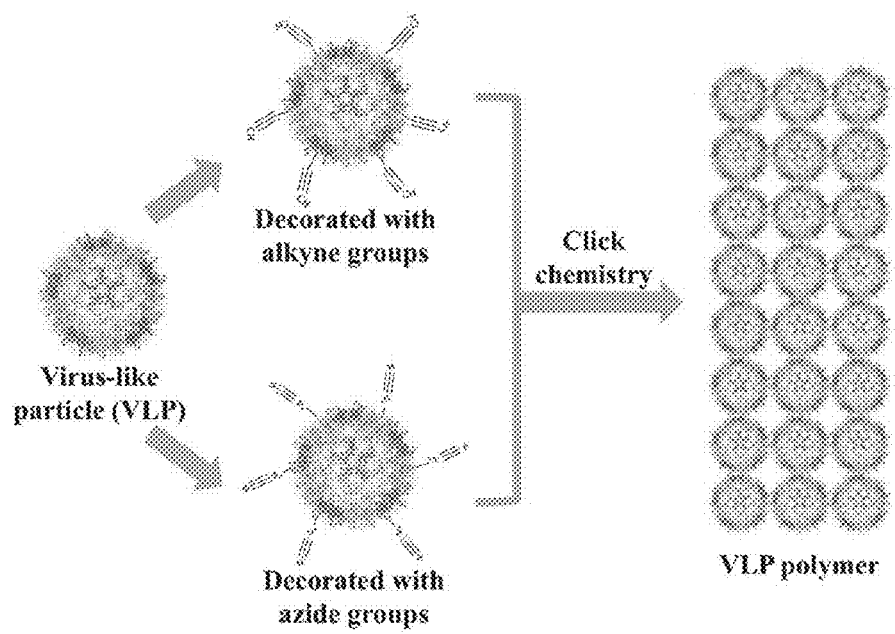
FIG. 9: Illustrative diagram of the VLP polymerization.

HBc capsid protein truncated at V149 was used. A CFPS method was used for producing HBc capsid protein. The truncated HBc protein self-assembles into VLPs, composed of 240 subunits arranged with T=4 icosahedral symmetry. Non-natural amino acids with azide groups or alkyne groups were introduced into the HBc capsid protein so that the new moieties would be displayed on the VLP surface. The VLP was further stabilized by introducing disulfide bridges (D29C-R127C) throughout the capsid. VLPs were then polymerized by click chemistry to interconnect the VLPs. The diagram is shown in FIG. 9.

Figure 10:
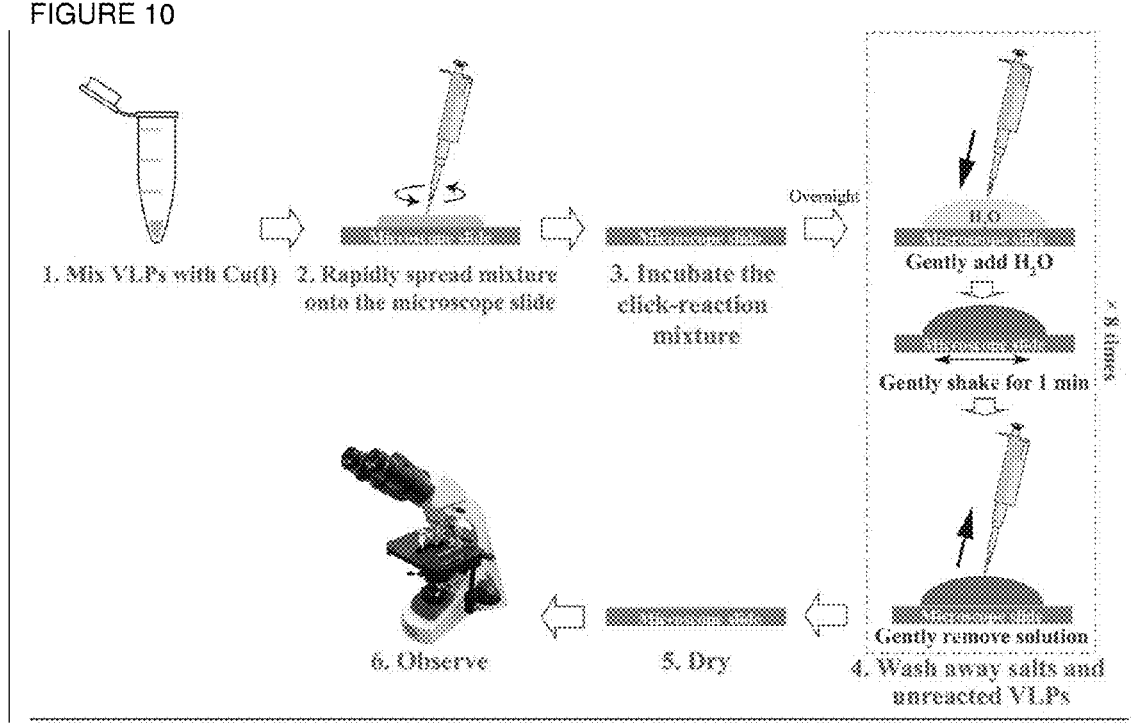
FIG. 10. Polymerization of VLPs
Figure 11:
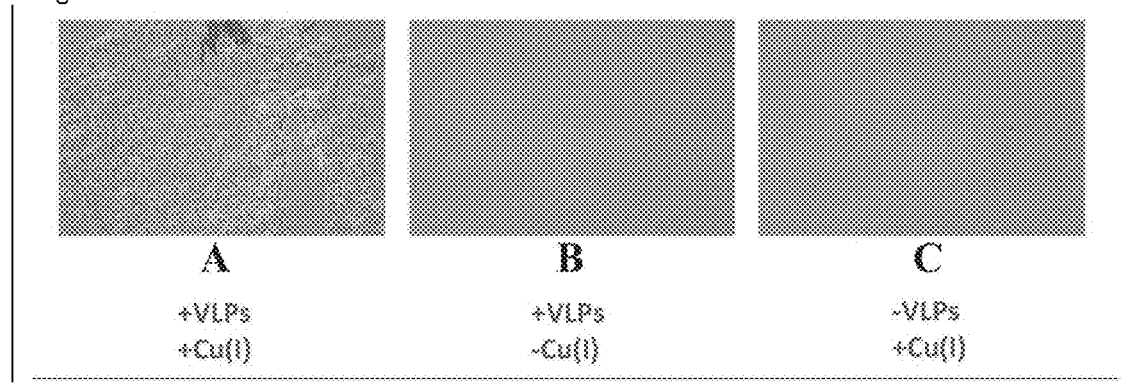
FIG. 11. Microscopic image of the VLP polymer (A). The controls are: with VLPs but without the Cu(I) conjugation catalyst (B) and without VLPs (C). Both controls showed no retention of material. The photographs were taken at 10× magnification.

All the conjugation reactions were done in an anaerobic glove box to stabilize the Cu(I) catalyst while avoiding the need for reducing agents that can break the disulfide bonds used to stabilize the VLPs. As shown in FIG. 10, HBc VLP solutions (VLP(azide):VLP(alkyne)=1:1) were mixed with 1 mM Tetrakis Cu(I) catalyst and then rapidly spread on the microscope slide. Reactions without VLPs and without Cu(I) were controls. After incubating the click chemistry reactions overnight, the slide surfaces were washed 8 times using water to remove salts and unreacted VLPs. The slides were then observed under a 10× power optical microscope after they were dry. Microscopic observation showed that the VLPs were successfully polymerized and retained on the microscope slide after the click reaction, as shown in FIG. 11.

Materials and Methods

Plasmid Construction.

The sequence encoding the human Hepatitis B core (HBc) capsid monomer of subtype adyw (Pasek et al., 1979) with the C-terminus truncated at amino acid 149 was optimized to avoid the need for rare *E. coli* tRNAs and was synthesized from oligonucleotides designed with DNAworks v3.0. The vector pET24a-HBc149 was generated by ligation (T4 DNA ligase, New England Biolabs, Ipswich, Mass.) of the optimized HBc protein gene into the pET-24a(+) vector (Novagen, San Diego, Calif.) at the Nde I and Xho I restriction sites. To incorporate methionine analogues on the VLP surfaces and not into the central structure of the capsid protein, two mutations (M66S and L76M) were introduced. To stabilize the VLP, two mutations (D29C and R127C) were introduced. The plasmid was transformed into DH5a cells and purified with Qiagen Plasmid Maxi Kit (Qiagen, Valencia, Calif.) for use in cell-free protein synthesis (CFPS). All mutants were constructed using QuikChange PCR (Stratagene, La Jolla, Calif.).

Sequences of HBc protein variants. The sequences of wild-type, HBc(azide) and HBc(alkyne) are shown in the table below. AHA signifies azidohomoalanine, the non-natural amino with an azide group. HPG signifies homopropargylglycine, the non-natural amino with an alkyne group.

| Variants | Protein sequence | DNA encoding sequence |
|---|---|---|
| Wild-type (HBc149) | (SEQ ID NO: 1)<br>MDIDPYKEFGATVELL<br>SFLPSDFFPSVRDLLD<br>TAAALYRDALESPEHC<br>SPHHTALRQAILCWGD<br>LMTLATWVGTNLEDPA<br>SRDLVVSYVNTNVGLK<br>FRQLLWFHISCLTFGR<br>ETVLEYLVSFGVWIRT<br>PPAYRPPNAPILSTLP<br>ETTVV | (SEQ ID NO: 2)<br>ATGGATATCGACCCGTACAAA<br>GAATTCGGCGCGACCGTTGAA<br>CTGCTGTCTTTCCTGCCGTCT<br>GATTTCTTCCCGTCTGTTCGT<br>GACCTGCTGGACACCGCGGCA<br>GCACTGTACCGTGACGCGCTG<br>GAATCTCCGGAACATTGTTCT<br>CCGCATCACACTGCGCTGCGT<br>CAGGCGATTCTGTGCTGGGGC<br>GACCTGATGACCCTGGCGACT<br>TGGGTTGGCACCAACCTGGAA<br>GATCCGGCGTCTCGTGATCTG<br>GTTGTTTCTTACGTTAACACT<br>AACGTTGGTCTGAAATTCCGT<br>CAGCTGCTGTGGTTCCACATC<br>TCTTGCCTGACCTTCGGTCGT<br>GAAACCGTTCTGGAATACCTG<br>GTTTCTTTTGGTGTTTGGATT<br>CGTACTCCGCCGGCTTACCGT<br>CCGCCGAACGCACCGATCCTG<br>AGCACCCTGCCGGAAACCACT<br>GTTGTGTAATAA |
| HBc (azide) | (SEQ ID NO: 3)<br>MDIDPYKEFGATVELL<br>SFLPSDFFPSVRCLLD<br>TAAALYRDALESPEHC<br>SPHHTALRQAILCWGD<br>LSTLATWVGTN(AHA)<br>EDPASRDLVVSYVNTN<br>VGLKFRQLLWFHISCL<br>TFGRETVLEYLVSFGV<br>WICTPPAYRPPNAPIL<br>STLPETTVV | (SEQ ID NO: 4)<br>ATGGATATCGACCCGTACAAA<br>GAATTCGGCGCGACCGTTGAA<br>CTGCTGTCTTTCCTGCCGTCT<br>GATTTCTTCCCGTCTGTTCGT<br>TGCCTGCTGGACACCGCGGCA<br>GCACTGTACCGTGACGCGCTG<br>GAATCTCCGGAACATTGTTCT<br>CCGCATCACACTGCGCTGCGT<br>CAGGCGATTCTGTGCTGGGGC<br>GACCTGagcACCCTGGCGACT<br>TGGGTTGGCACCAACatgGAA<br>GATCCGGCGTCTCGTGATCTG<br>GTTGTTTCTTACGTTAACACT<br>AACGTTGGTCTGAAATTCCGT<br>CAGCTGCTGTGGTTCCACATC<br>TCTTGCCTGACCTTCGGTCGT<br>GAAACCGTTCTGGAATACCTG<br>GTTTCTTTTGGTGTTTGGATT<br>TGTACTCCGCCGGCTTACCGT<br>CCGCCGAACGCACCGATCCTG<br>AGCACCCTGCCGGAAACCACT<br>GTTGTGTAATAA |
| HBc (alkyne) | (SEQ ID NO: 5)<br>MDIDPYKEFGATVELL<br>SFLPSDFFPSVRCLLD<br>TAAALYRDALESPEHC<br>SPHHTALRQAILCWGD<br>LSTLATWVGTN(HPG)<br>EDPASRDLVVSYVNTN<br>VGLKFRQLLWFHISCL<br>TFGRETVLEYLVSFGV<br>WICTPPAYRPPNAPIL<br>STLPETTVV | (SEQ ID NO: 6)<br>ATGGATATCGACCCGTACAAA<br>GAATTCGGCGCGACCGTTGAA<br>CTGCTGTCTTTCCTGCCGTCT<br>GATTTCTTCCCGTCTGTTCGT<br>TGCCTGCTGGACACCGCGGCA<br>GCACTGTACCGTGACGCGCTG<br>GAATCTCCGGAACATTGTTCT<br>CCGCATCACACTGCGCTGCGT<br>CAGGCGATTCTGTGCTGGGGC<br>GACCTGagcACCCTGGCGACT<br>TGGGTTGGCACCAACatgGAA<br>GATCCGGCGTCTCGTGATCTG<br>GTTGTTTCTTACGTTAACACT<br>AACGTTGGTCTGAAATTCCGT<br>CAGCTGCTGTGGTTCCACATC<br>TCTTGCCTGACCTTCGGTCGT<br>GAAACCGTTCTGGAATACCTG<br>GTTTCTTTTGGTGTTTGGATT<br>TGTACTCCGCCGGCTTACCGT<br>CCGCCGAACGCACCGATCCTG<br>AGCACCCTGCCGGAAACCACT<br>GTTGTGTAATAA |

Cell-free protein synthesis (CFPS). CFPS was conducted using the PANOx-SP (PEP, amino acids, nicotinamide adenine dinucleotide (NAD), oxalic acid, spermidine, and putrescine) cell-free system as described previously (Jewett and Swartz 2004) with several modifications. The standard PANOx-SP CFPS reaction mixture includes: 1.2 mM ATP, 0.85 mM each of GTP, UTP, and CTP, 33 mM phosphoenol pyruvate (Roche Molecular Biochemicals, Indianapolis, Ind.), 170 mM potassium glutamate, 10 mM ammonium glutamate, 16 mM magnesium glutamate, 1.5 mM spermidine, 1.0 mM putrescine, 0.17 mg/mL folinic acid, 45 µg/mL plasmid, approximately 100-300 µg/mL T7 RNA polymerase, 2 mM of each of the 20 unlabeled amino acids, 0.33 mM NAD, 0.26 mM Coenzyme A (CoA), 2.7 mM potassium oxalate, and 0.28 volumes of *E. coli* KC6 S30 extract (Goerke and Swartz 2008). For global replacement of methionines in HBc proteins, methionine was left out of cell-free reaction mixtures, and substituted by 1 mM azidohomoalanine (AHA) (Medchem Source LLP, Federal Way, Wash.) or 1 mM homopropargylglycine (HPG) (Chiralix B.V., Nijmegen, The Netherlands). All reagents were obtained from Sigma-Aldrich (St. Louis, Mo.) unless otherwise noted.

CFPS reactions to produce the HBc protein were conducted at 30° C. for 6 h. Small-scale CFPS reactions were carried out in 20 µL volumes in 1.5 mL microcentrifuge tubes. Preparative-scale reactions used 6 mL volumes with 1 mL per well in 6-well tissue culture plates (BD Falcon #3046, BD, Franklin Lakes, N.J.).

VLP purification. The cell-free product was immediately dialyzed in 6-8000 MWCO Specra/Pro Molecularporous Membrane Tubing (Spectrum Labs, Rancho Dominguez, Calif.) against Dialysis Buffer (10 mM Tris-HCl, pH 7.4, 0.5 M NaCl) with 1 mM DTT with 2 buffer exchanges. The dialyzed cell-free reaction product was loaded on an SEC (size-exclusion chromatography) column packed with Sepharose 6 FastFlow resin (GE Healthcare). The running buffer is as the dialysis buffer. The isolated VLPs from SEC were oxidized to form disulfide bonds by adding 20 mM diamide and incubating at room temperature for 6 h. The oxidants were removed by dialysis against the Dialysis Buffer with 2 buffer exchanges.

Azide-Alkyne Conjugation.

The [3+2] cycloaddition click reactions were conducted in an anaerobic glove box (Coy Laboratories, Grass Lake, Mich.) to preserve the reduced state of the tetrakis(acetonitrile)copper(I)hexafluorophosphate catalyst ([(CH3CN)4Cu] PF6 (Sigma Aldrich, St. Louis, Mo.). HBc VLPs with azide groups were mixed with HBc VLPs with alkyne groups (1:1 molar ratio) and the resulting solution was moved into the anaerobic glove box. Both solutions contained 20 mM potassium phosphate buffer at pH 8 and 0.01% Tween 20. After 2 hours, the VLP solutions were mixed with the Cu(I) catalyst to reach a catalyst concentration of 1 mM and then quickly spread on the surface of a clean microscope slide. The reactions without VLPs or Cu(I) were conducted as controls. After overnight incubation at room temperature, the slide surfaces were washed 8 times with water to remove salts and unreacted VLPs. After the slides were dry, they were observed under a Nikon Eclipse TE300 microscope at 10× magnification and photographs were taken.

Wang et al. *Annual Review of Biophysics and Biomolecular Structure* 2006, 35, 225-249.

Magliery *Medicinal Chemistry Reviews—Online* 2005, 2, 303-323.

Pédelacq et al. *Nature Biotechnology* 2006, 24, 79-88.

Wang et al. *Journal of the American Chemical Society* 2003, 125, 3192-3193.

Albayrak, C.; Swartz, J. R. *Biochemical and Biophysical Research Communications* 2013, 431, 291-295.

Bundy, B. C.; Swartz, J. R. *Bioconjugate Chemistry* 2010, 21, 255-263.

Goerke, A. R.; Swartz, J. R. *Biotechnology and Bioengineering* 2009, 102, 400-416.

Jewett, M. C.; Swartz, J. R. *Biotechnology and Bioengineering* 2004, 86, 19-26.

Calhoun, K. A.; Swartz, J. R. *Journal of Biotechnology* 2006, 123, 193-203.

Michel-Reydellet, N.; Calhoun, K.; Swartz, *J. Metabolic Engineering* 2004, 6, 197-203.

Goerke, A. R.; Swartz, J. R. *Biotechnology and Bioengineering* 2008, 99, 351-367.

Calhoun, K. A.; Swartz, J. R. *Biotechnology Progress* 2005, 21, 1146-1153.

Budyka, M. F. *High Energy Chemistry* 2007, 41, 176-187.

Adzima, B. J.; Tao, Y.; Kloxin, C. J.; DeForest, C. A.; Anseth, K. S.; Bowman, C. N. *Nature Chemistry* 2011, 3, 258-261.

Hudalla, G. A.; Murphy, W. L. *Advanced Functional Materials* 2011, 21, 1754-1768.

Dueber, J. E.; Wu, G. C.; Malmirchegini, G. R.; Moon, T. S.; Petzold, C. J.; Ullal, A. V; Prather, K. L. J.; Keasling, J. D. *Nature Biotechnology* 2009, 27, 753-759.

Baskin et al. *Proceedings of the National Academy of Sciences of the United States of America* 2007, 104, 16793-16797.

Codelli et al. *Journal of the American Chemical Society* 2008, 130, 11486-11493.

Laughlin et al. *Science* (New York, N.Y.) 2008, 320, 664-667.

Cho et al. *Proceedings of the National Academy of Sciences of the United States of America* 2011, 108, 9060-9065.

Saxon, E.; Bertozzi, C. *Science* 2000, 287, 2007-2010.

Nguyen et al. *Journal of the American Chemical Society* 2009, 131, 8720-8721.

Nguyen et al. *Journal of the American Chemical Society* 2011, 133, 11418-11421.

Plass et al. *Angewandte Chemie* (International ed. in English) 2011, 50, 3878-3881.

Zawada et al. *Biotechnology and Bioengineering* 2011, 108, 1570-1578.

It is to be understood that this invention is not limited to the particular methodology, protocols, cell lines, animal species or genera, constructs, and reagents described, as such may, of course, vary. It is also to be understood that the terminology used herein is for the purpose of describing particular embodiments only, and is not intended to limit the scope of the present invention, which will be limited only by the appended claims.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

What is claimed is:

1. A method for synthesis of a multimeric structure, the method comprising:
    reacting in a bioorthogonal reaction:
        two polypeptide subunit monomers, each comprising two first non-natural amino acids with two second subunit monomers, each comprising two second non-natural amino acids; and
    coupling covalently, the two first subunits with the two second subunits by forming covalent linkages between the first and second nonnatural amino acids, thereby synthesizing a multimeric structure.

2. The method of claim 1, wherein two different non-natural amino acids are present on the first polypeptide subunit monomers.

3. The method of claim 1, wherein different non-natural amino acids are present on the first and second subunit monomers.

4. The method of claim 1, wherein at least one unnatural amino acid is present on a polypeptide and bioorthogonal reactive moiety is present in a polymer subunit other than a polypeptide.

5. The method of claim 1, wherein at least one non-natural amino acid is selected from the group consisting of—p-acetyl-L-phenylalanine, p-azido-L-phenylalanine and p-propargyloxy-L-phenylalanine (pPaF).

6. The method of claim 1, wherein the multimeric structure is a linear or branched polymer.

7. The method of claim 1, wherein the multimeric structure is a planar array.

8. The method of claim 1, wherein the multimeric structure comprises covalently linked icosahedral assemblies.

9. The method of claim 8, wherein the icosahedral assembly is a virus-like particle.

10. The method of claim 9, wherein the virus-like particles comprises hepatitis B virus core protein.

11. A multimeric structure comprising a plurality of covalently linked polypeptide icosahedral assemblies.

12. The multimeric structure of claim 11, wherein the covalent linkage is generated by bioorthogonal reactions between non-natural amino acids.

13. The multimeric structure of claim 12, wherein the icosahedral structures are virus-like particles (VLPs).

14. The multimeric structure of claim 13, wherein the VLPs are stabilized by covalent bonds.

15. The multimeric structure of claim 14, wherein the VLPs are comprised of hepatitis B virus core protein.

16. The method of claim 1 wherein covalently coupling comprises covalently linking the first and second non-natural amino acids with a linker.

17. A multimeric structure comprising:
    a polymer comprising:
    first polypeptide subunit monomers comprising at least two first nonnatural amino acids; and
    second subunit monomers comprising at least two second nonnatural amino acids
    wherein the first monomers are covalently linked to the second monomers by linkages between first and second nonnatural amino acids.

18. The multimeric structure of claim 17 wherein the multimeric structure is a linear polymer, a branched polymer, a planar array, or a three-dimensional structure.

19. The multimeric structure of claim 17 wherein the multimeric structure comprises one or more polypeptide subunits linked by a small molecule polymer.

20. The multimeric structure of claim 19 wherein the small molecule polymer comprises polyethylene glycol.

* * * * *